US010524900B2

(12) United States Patent
Beer

(10) Patent No.: US 10,524,900 B2
(45) Date of Patent: Jan. 7, 2020

(54) ACCOMMODATIVE INTRAOCULAR LENS AND METHOD OF IMPROVING ACCOMMODATION

(71) Applicant: Z Lens, LLC, Slingerlands, NY (US)

(72) Inventor: Paul M. Beer, Slingerlands, NY (US)

(73) Assignee: Z Lens, LLC, St. Petersburg, FL (US)

( * ) Notice: Subject to any disclaimer, the term of this patent is extended or adjusted under 35 U.S.C. 154(b) by 437 days.

(21) Appl. No.: 14/934,962

(22) Filed: Nov. 6, 2015

(65) Prior Publication Data

US 2016/0157995 A1    Jun. 9, 2016

Related U.S. Application Data

(62) Division of application No. 13/157,703, filed on Jun. 10, 2011, now Pat. No. 9,220,590.

(Continued)

(51) Int. Cl.
*A61F 2/16* (2006.01)
*A61F 9/007* (2006.01)

(52) U.S. Cl.
CPC .......... *A61F 2/1624* (2013.01); *A61F 2/1616* (2013.01); *A61F 2/1629* (2013.01);
(Continued)

(58) Field of Classification Search
CPC ........ A61F 2/16; A61F 2/1613; A61F 2/1629; A61F 2002/1681; A61F 2002/1682;
(Continued)

(56) References Cited

U.S. PATENT DOCUMENTS 3,975,779 A    8/1976   Richards et al.
3,991,426 A    11/1976  Flom et al.
(Continued)

FOREIGN PATENT DOCUMENTS

AU    2003294418 A1    6/2004
AU    2003297101 A1    6/2004
(Continued)

OTHER PUBLICATIONS

International Preliminary Report on Patentability and Written Opinion dated Nov. 20, 2014 in International Application No. PCT/US2013/039708 (13 pages).
International Search Report and Written Opinion dated Dec. 4, 2013 in International Application No. PCT/US2013/039708 (18 pages).
Invitation to Pay Additional Fees dated Sep. 17, 2013 in International Application No. PCT/US2013/039708 (8 pages).
U.S. Appl. No. 13/157,703, filed Jun. 10, 2011 by Paul Marius Beer.
Non-Final Office Action in U.S. Appl. No. 13/157,703 dated Jul. 25, 2014.
Notice of Allowance in U.S. Appl. No. 13/157,703 dated Oct. 8, 2015.

(Continued)

*Primary Examiner* — Suba Ganesan
(74) *Attorney, Agent, or Firm* — Goodwin Procter LLP

(57) ABSTRACT

The present invention provides an accommodative intraocular lens (AIOL) system and method for improving accommodation with an intraocular lens. The method involves insertion into the capsular bag of a flexible optic holder comprising a plurality of haptics configured to allow the capsular bag to be sectioned at regular intervals following fusion of the capsular bag. The haptics of the optic holder are designed to allow maximum fusion of the anterior and posterior leaves of the capsular bag following placement of the optic holder in the capsular bag. Following introduction of the optic holder into the capsular bag, the natural or assisted process of fibrosis/fusion of the capsular bag occurs, thereby sealing and securely capturing the haptics within the capsular bag. Subsequently, several cuts are made in the fibrotic capsular bag at intervals between haptics, allowing the haptics to move independently, thereby effectively restoring some of the flexibility that the capsule possessed prior to fibrosis and restoring some of the zonular force on the capsule.

12 Claims, 13 Drawing Sheets

Related U.S. Application Data

(60) Provisional application No. 61/353,273, filed on Jun. 10, 2010, provisional application No. 61/368,862, filed on Jul. 29, 2010.

(52) U.S. Cl.
CPC ............ *A61F 2/1648* (2013.01); *A61F 9/007* (2013.01); *A61F 2002/1681* (2013.01); *A61F 2002/1699* (2015.04); *A61F 2002/16901* (2015.04)

(58) Field of Classification Search
CPC ...... A61F 2002/1683; A61F 2002/1689; A61F 2002/16901; A61F 2002/16903
See application file for complete search history.

(56) References Cited

U.S. PATENT DOCUMENTS

| | | |
|---|---|---|
| 4,053,953 A | 10/1977 | Flom et al. |
| 4,056,855 A | 11/1977 | Kelman |
| 4,124,905 A | 11/1978 | Clark |
| 4,262,370 A | 4/1981 | Hartstein |
| 4,373,218 A | 2/1983 | Schachar |
| 4,463,457 A | 8/1984 | Kelman |
| 4,527,294 A | 7/1985 | Heslin |
| 4,534,069 A | 8/1985 | Kelman |
| 4,575,373 A | 3/1986 | Johnson |
| 4,581,032 A | 4/1986 | Grandon |
| 4,581,033 A | 4/1986 | Callahan |
| 4,588,406 A | 5/1986 | Fedorov et al. |
| 4,666,446 A | 5/1987 | Koziol et al. |
| 4,685,922 A | 8/1987 | Peyman |
| 4,693,717 A | 9/1987 | Michelson |
| 4,718,904 A | 1/1988 | Thornton |
| 4,738,680 A | 4/1988 | Herman |
| 4,781,719 A | 11/1988 | Kelman |
| 4,787,903 A | 11/1988 | Grendahl |
| 4,790,847 A | 12/1988 | Woods |
| 4,842,601 A | 6/1989 | Smith |
| 4,871,363 A | 10/1989 | Kelman |
| 4,878,910 A | 11/1989 | Koziol et al. |
| 4,888,012 A | 12/1989 | Horn et al. |
| 4,888,015 A | 12/1989 | Domino |
| 4,892,543 A | 1/1990 | Turley |
| 4,932,966 A | 6/1990 | Christie et al. |
| 4,932,968 A | 6/1990 | Caldwell et al. |
| 4,936,850 A | 6/1990 | Barrett |
| 4,944,082 A | 7/1990 | Jones et al. |
| 4,950,288 A | 8/1990 | Kelman |
| 4,955,894 A | 9/1990 | Herman |
| 4,963,148 A | 10/1990 | Sulc et al. |
| 4,995,879 A | 2/1991 | Dougherty |
| 5,104,590 A | 4/1992 | Blake |
| 5,108,429 A | 4/1992 | Wiley |
| 5,185,107 A | 2/1993 | Blake |
| 5,192,319 A | 3/1993 | Worst |
| RE34,424 E | 10/1993 | Walman |
| 5,282,851 A | 2/1994 | Jacob-LaBarre |
| 5,288,293 A | 2/1994 | O'Donnell, Jr. |
| 5,306,297 A | 4/1994 | Rheinish et al. |
| 5,326,347 A | 7/1994 | Cumming |
| 5,366,500 A | 11/1994 | Schneider et al. |
| 5,423,929 A | 6/1995 | Doyle et al. |
| 5,476,514 A | 12/1995 | Cumming |
| 5,489,302 A | 2/1996 | Skottun |
| 5,496,366 A | 3/1996 | Cumming |
| 5,507,806 A | 4/1996 | Blake |
| 5,527,415 A | 6/1996 | Doyle et al. |
| 5,549,668 A | 8/1996 | O'Donnell, Jr. |
| 5,562,731 A | 10/1996 | Cumming |
| 5,571,177 A | 11/1996 | Deacon et al. |
| 5,578,081 A | 11/1996 | McDonald |
| 5,593,436 A | 1/1997 | Langerman |
| 5,607,472 A | 3/1997 | Thompson |
| 5,674,282 A | 10/1997 | Cumming |
| 5,683,456 A | 11/1997 | Blake |
| 5,702,441 A | 12/1997 | Zhou |
| 5,728,155 A | 3/1998 | Anello et al. |
| 5,728,156 A | 3/1998 | Gupta et al. |
| 5,769,889 A | 6/1998 | Kelman |
| 5,782,911 A | 7/1998 | Herrick |
| 5,800,532 A | 9/1998 | Lieberman |
| 5,803,925 A | 9/1998 | Yang et al. |
| 5,843,187 A | 12/1998 | Bayers |
| 5,855,605 A | 1/1999 | Herrick |
| 5,964,802 A | 10/1999 | Anello et al. |
| 5,984,962 A | 11/1999 | Anello et al. |
| 6,013,101 A | 1/2000 | Israel |
| 6,015,435 A | 1/2000 | Valunin et al. |
| 6,027,531 A | 2/2000 | Tassignon |
| 6,048,364 A | 4/2000 | Skottun |
| 6,051,024 A | 4/2000 | Cumming |
| 6,053,944 A | 4/2000 | Tran et al. |
| 6,083,261 A | 7/2000 | Callahan et al. |
| 6,096,077 A | 8/2000 | Callahan et al. |
| 6,096,078 A | 8/2000 | McDonald |
| 6,110,202 A | 8/2000 | Barraquer et al. |
| 6,139,576 A | 10/2000 | Doyle et al. |
| 6,143,027 A | 11/2000 | Ratner et al. |
| 6,152,959 A | 11/2000 | Portney |
| 6,171,337 B1 | 1/2001 | Galin |
| 6,176,878 B1 | 1/2001 | Gwon et al. |
| 6,179,843 B1 | 1/2001 | Weiler |
| 6,190,410 B1 | 2/2001 | Lamielle et al. |
| 6,197,058 B1 | 3/2001 | Portney |
| 6,197,059 B1 | 3/2001 | Cumming |
| 6,200,342 B1 | 3/2001 | Tassignon |
| 6,200,344 B1 | 3/2001 | Lamielle et al. |
| 6,217,612 B1 | 4/2001 | Woods |
| 6,224,628 B1 | 5/2001 | Callahan et al. |
| 6,228,115 B1 | 5/2001 | Hoffmann et al. |
| 6,241,777 B1 | 6/2001 | Kellan |
| 6,251,312 B1 | 6/2001 | Phan et al. |
| 6,261,321 B1 | 7/2001 | Kellan |
| 6,280,449 B1 | 8/2001 | Blake |
| 6,299,641 B1 | 10/2001 | Woods |
| 6,302,912 B1 | 10/2001 | Bernau |
| 6,306,167 B1 | 10/2001 | Bernau et al. |
| 6,358,280 B1 | 3/2002 | Herrick |
| 6,387,126 B1 | 5/2002 | Cumming |
| 6,398,809 B1 | 6/2002 | Hoffmann et al. |
| 6,406,494 B1 | 6/2002 | Laguette et al. |
| 6,413,262 B2 | 7/2002 | Saishin et al. |
| 6,413,277 B1 | 7/2002 | Neuhann |
| 6,423,094 B1 | 7/2002 | Sarfarazi |
| 6,425,917 B1 | 7/2002 | Blake |
| 6,428,574 B1 | 8/2002 | Valunin et al. |
| 6,432,246 B1 | 8/2002 | Blake |
| 6,443,984 B1* | 9/2002 | Jahn ................ A61F 2/1629 623/6.22 |
| 6,443,985 B1 | 9/2002 | Woods |
| 6,451,056 B1 | 9/2002 | Cumming |
| 6,461,384 B1 | 10/2002 | Hoffmann et al. |
| 6,464,725 B2 | 10/2002 | Skotton |
| 6,475,240 B1 | 11/2002 | Paul |
| 6,482,229 B1 | 11/2002 | Gwon et al. |
| 6,488,707 B1 | 12/2002 | Callahan et al. |
| 6,488,708 B2 | 12/2002 | Sarfarazi |
| 6,488,709 B1 | 12/2002 | Barrett |
| 6,494,911 B2 | 12/2002 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,537,317 B1 | 3/2003 | Steinert et al. |
| 6,543,453 B1 | 4/2003 | Klima et al. |
| 6,547,822 B1 | 4/2003 | Lang |
| 6,554,859 B1 | 4/2003 | Lang et al. |
| 6,558,395 B2 | 5/2003 | Hjertman et al. |
| 6,558,420 B2 | 5/2003 | Green |
| 6,576,012 B2 | 6/2003 | Lang |
| 6,592,621 B1 | 7/2003 | Domino |
| 6,596,025 B2 | 7/2003 | Portney |
| 6,605,093 B1 | 8/2003 | Blake |

(56) References Cited

U.S. PATENT DOCUMENTS

| | | |
|---|---|---|
| 6,616,692 B1 | 9/2003 | Glick et al. |
| 6,638,306 B2 | 10/2003 | Cumming |
| 6,660,035 B1 | 12/2003 | Lang et al. |
| 6,666,887 B1 | 12/2003 | Callahan et al. |
| 6,695,881 B2 | 2/2004 | Peng et al. |
| 6,749,634 B2 | 6/2004 | Hanna |
| 6,755,859 B2 | 6/2004 | Hoffmann et al. |
| 6,761,737 B2 | 7/2004 | Zadno-Azizi et al. |
| 6,764,511 B2 | 7/2004 | Zadno-Azizi et al. |
| 6,767,363 B1 | 7/2004 | Bandhauer et al. |
| 6,786,928 B2 | 9/2004 | Callahan et al. |
| 6,786,934 B2 | 9/2004 | Zadno-Azizi et al. |
| 6,790,232 B1 | 9/2004 | Lang |
| 6,797,003 B1 | 9/2004 | Blake et al. |
| 6,800,091 B2 | 10/2004 | Callahan et al. |
| 6,824,563 B2 | 11/2004 | Lang |
| 6,846,326 B2 | 1/2005 | Zadno-Azizi et al. |
| 6,849,091 B1 | 2/2005 | Cumming |
| 6,855,164 B2 | 2/2005 | Glazier |
| 6,858,040 B2 | 2/2005 | Nguyen et al. |
| 6,884,261 B2 | 4/2005 | Zadno-Azizi et al. |
| 6,899,732 B2 | 5/2005 | Zadno-Azizi et al. |
| 6,918,930 B2 | 7/2005 | Portney |
| 6,921,415 B2 | 7/2005 | Callahan et al. |
| 6,921,416 B2 | 7/2005 | Khoury |
| 6,926,736 B2 | 8/2005 | Peng et al. |
| 6,926,744 B1 | 8/2005 | Bos et al. |
| 6,932,839 B1 | 8/2005 | Kamerling et al. |
| 6,969,403 B2 | 11/2005 | Peng et al. |
| 6,986,763 B2 | 1/2006 | Holmen |
| 6,986,787 B1 | 1/2006 | Baker, Jr. |
| 6,991,651 B2 | 1/2006 | Portney |
| 7,025,783 B2 | 4/2006 | Brady et al. |
| 7,036,931 B2 | 5/2006 | Lindacher et al. |
| 7,037,338 B2 | 5/2006 | Nagamoto |
| 7,041,134 B2 | 5/2006 | Nguyen et al. |
| 7,048,759 B2 | 5/2006 | Bogaert et al. |
| 7,048,760 B2 | 5/2006 | Cumming |
| 7,060,094 B2 | 6/2006 | Shahinpoor et al. |
| 7,063,723 B2 | 6/2006 | Ran |
| 7,087,080 B2 | 8/2006 | Zadno-Azizi et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,122,053 B2 | 10/2006 | Esch |
| 7,125,422 B2 | 10/2006 | Woods et al. |
| 7,137,702 B2 | 11/2006 | Piers et al. |
| 7,150,759 B2 | 12/2006 | Paul et al. |
| 7,150,760 B2 | 12/2006 | Zhang |
| 7,192,444 B2 | 3/2007 | Blake et al. |
| 7,198,640 B2 | 4/2007 | Nguyen |
| 7,204,849 B2 | 4/2007 | Portney |
| 7,217,288 B2 | 5/2007 | Esch et al. |
| 7,220,279 B2 | 5/2007 | Nun |
| 7,226,478 B2 | 6/2007 | Ting et al. |
| 7,229,475 B2 | 6/2007 | Glazier |
| 7,238,201 B2 | 7/2007 | Portney et al. |
| 7,247,168 B2 | 7/2007 | Esch et al. |
| 7,261,737 B2 | 8/2007 | Esch et al. |
| 7,354,451 B2 | 4/2008 | Koch |
| 7,377,640 B2 | 5/2008 | Piers et al. |
| 7,381,221 B2 | 6/2008 | Lang et al. |
| 7,384,429 B2 | 6/2008 | Hanna |
| 7,404,637 B2 | 7/2008 | Miller et al. |
| 7,404,638 B2 | 7/2008 | Miller et al. |
| 7,435,259 B2 | 10/2008 | Cumming |
| 7,452,362 B2 | 11/2008 | Zadno-Azizi et al. |
| 7,452,378 B2 | 11/2008 | Zadno-Azizi et al. |
| 7,455,691 B2 | 11/2008 | Feingold et al. |
| 7,462,193 B2 | 12/2008 | Nagamoto |
| 7,485,144 B2 | 2/2009 | Esch |
| 7,494,505 B2 | 2/2009 | Kappelhof et al. |
| 7,503,938 B2 * | 3/2009 | Phillips ............... A61F 2/1629 623/6.11 |
| 7,553,327 B2 | 6/2009 | Cumming |
| 7,569,073 B2 | 8/2009 | Vaudant et al. |
| 7,591,849 B2 | 9/2009 | Richardson |
| 7,601,169 B2 | 10/2009 | Phillips |
| 7,615,056 B2 | 11/2009 | Ayton et al. |
| 7,615,073 B2 | 11/2009 | Deacon et al. |
| 7,621,949 B2 | 11/2009 | Deacon et al. |
| 7,637,947 B2 | 12/2009 | Smith et al. |
| 7,662,179 B2 | 2/2010 | Sarfarazi |
| 7,670,371 B2 | 3/2010 | Piers et al. |
| 7,674,288 B2 | 3/2010 | Nagamoto |
| 7,713,299 B2 | 5/2010 | Brady et al. |
| 7,722,670 B2 | 5/2010 | Elahi et al. |
| 7,744,646 B2 | 6/2010 | Zadno-Azizi et al. |
| 7,744,647 B2 | 6/2010 | Barrett |
| 7,763,069 B2 | 7/2010 | Brady et al. |
| 7,763,070 B2 | 7/2010 | Cumming |
| 7,771,471 B2 | 8/2010 | Dell |
| 7,780,729 B2 | 8/2010 | Nguyen et al. |
| 7,790,824 B2 | 9/2010 | Freeman |
| 7,790,825 B2 | 9/2010 | Lehman et al. |
| 7,794,497 B2 | 9/2010 | Brady et al. |
| 7,794,498 B2 | 9/2010 | Pinchuk |
| 7,806,930 B2 | 10/2010 | Brown |
| 7,811,320 B2 | 10/2010 | Werblin |
| 7,815,678 B2 | 10/2010 | Ben Nun |
| 7,837,730 B2 | 11/2010 | Cumming et al. |
| 7,842,087 B2 | 11/2010 | Ben Nun |
| 7,854,764 B2 | 12/2010 | Ben Nun |
| 7,857,850 B2 | 12/2010 | Mentak et al. |
| 7,871,437 B2 | 1/2011 | Hermans et al. |
| 7,878,655 B2 | 2/2011 | Salvati et al. |
| 7,883,540 B2 | 2/2011 | Niwa et al. |
| 7,905,917 B2 | 3/2011 | Altmann |
| 7,931,686 B2 | 4/2011 | Vaudant et al. |
| 7,942,889 B2 | 5/2011 | Assia |
| 7,981,155 B2 | 7/2011 | Cumming |
| 7,985,253 B2 | 7/2011 | Cumming |
| 7,998,198 B2 | 8/2011 | Angelopoulos et al. |
| 7,998,199 B2 | 8/2011 | Ben Nun |
| 8,012,204 B2 | 9/2011 | Weinschenk, III et al. |
| 8,034,106 B2 | 10/2011 | Mentak et al. |
| 8,034,107 B2 | 10/2011 | Stenger |
| 8,034,108 B2 | 10/2011 | Bumbalough |
| 8,038,711 B2 | 10/2011 | Clarke |
| 8,043,370 B2 | 10/2011 | Bretthauer et al. |
| 8,043,372 B2 | 10/2011 | Bumbalough |
| 8,048,155 B2 | 11/2011 | Shadduck |
| 8,048,156 B2 | 11/2011 | Geraghty et al. |
| 8,052,752 B2 | 11/2011 | Woods et al. |
| 8,062,361 B2 | 11/2011 | Nguyen et al. |
| 8,062,362 B2 | 11/2011 | Brady et al. |
| 8,066,768 B2 | 11/2011 | Werblin |
| 8,066,769 B2 | 11/2011 | Werblin |
| 8,070,806 B2 | 12/2011 | Khoury |
| 8,080,017 B2 | 12/2011 | Tanaka |
| 8,100,965 B2 | 1/2012 | Cumming et al. |
| 8,109,998 B2 | 2/2012 | Cumming |
| 8,123,729 B2 | 2/2012 | Yamamoto et al. |
| 8,133,273 B2 | 3/2012 | Aharoni et al. |
| 8,158,712 B2 | 4/2012 | Your |
| 8,163,015 B2 | 4/2012 | Cumming |
| 8,167,941 B2 | 5/2012 | Boyd et al. |
| 8,182,531 B2 | 5/2012 | Hermans et al. |
| 8,187,325 B2 | 5/2012 | Zadno-Azizi et al. |
| 8,206,442 B2 | 6/2012 | Sel et al. |
| 8,215,770 B2 | 7/2012 | Blum et al. |
| 8,216,305 B2 | 7/2012 | Salvati et al. |
| 8,216,306 B2 | 7/2012 | Coroneo |
| 8,216,308 B2 | 7/2012 | Blake et al. |
| 8,231,672 B2 | 7/2012 | Deacon et al. |
| 8,235,525 B2 | 8/2012 | Lesage et al. |
| 8,241,353 B2 | 8/2012 | Deacon et al. |
| 8,241,355 B2 | 8/2012 | Brady et al. |
| 8,246,679 B2 | 8/2012 | Nguyen et al. |
| 8,267,996 B2 | 9/2012 | Niwa et al. |
| 8,273,123 B2 | 9/2012 | Ben Nun |
| 8,303,656 B2 | 11/2012 | Shadduck |
| 8,314,927 B2 | 11/2012 | Choi et al. |
| 8,328,869 B2 | 12/2012 | Smiley et al. |

(56) References Cited

U.S. PATENT DOCUMENTS

| | | | |
|---|---|---|---|
| 8,343,216 B2 | 1/2013 | Brady et al. |
| 8,343,217 B2 | 1/2013 | Bumbalough |
| 8,349,006 B2 | 1/2013 | Zhao et al. |
| 8,357,196 B2 | 1/2013 | Jain et al. |
| 8,361,145 B2 | 1/2013 | Scholl et al. |
| 8,366,653 B2 | 2/2013 | Shareef et al. |
| 8,377,123 B2 | 2/2013 | Evans et al. |
| 8,377,125 B2 | 2/2013 | Kellan |
| 8,382,831 B2 | 2/2013 | Ben Nun |
| 8,382,832 B2 | 2/2013 | Deacon et al. |
| 8,398,709 B2 | 3/2013 | Ben Nun |
| 8,403,984 B2 | 3/2013 | Tsai et al. |
| 8,414,646 B2 | 4/2013 | De Juan, Jr. et al. |
| 8,425,595 B2 | 4/2013 | Tsai et al. |
| 8,425,597 B2 | 4/2013 | Glick et al. |
| 8,425,598 B2 | 4/2013 | Klink et al. |
| 8,425,599 B2 | 4/2013 | Shadduck |
| 8,430,928 B2 | 4/2013 | Liao |
| 8,435,289 B2 | 5/2013 | Cole et al. |
| 8,449,611 B2 | 5/2013 | Richardson |
| 8,454,688 B2 | 6/2013 | Esch et al. |
| 8,465,544 B2 | 6/2013 | Brady et al. |
| 8,475,527 B2 | 7/2013 | Peterson et al. |
| 8,475,529 B2 | 7/2013 | Clarke |
| 8,480,734 B2 | 7/2013 | Kellan et al. |
| 8,486,140 B2 | 7/2013 | Willis et al. |
| 8,486,141 B2 | 7/2013 | Lang et al. |
| 8,486,142 B2 | 7/2013 | Bumbalough et al. |
| 8,496,701 B2 | 7/2013 | Hermans et al. |
| 8,500,804 B2 | 8/2013 | Brady et al. |
| 8,500,806 B1 | 8/2013 | Phillips |
| 8,523,942 B2 | 9/2013 | Cumming |
| 8,529,623 B2 | 9/2013 | Piers et al. |
| 8,535,376 B2 | 9/2013 | Altmann |
| 8,545,556 B2 | 10/2013 | Woods et al. |
| 8,551,164 B2 | 10/2013 | Willis et al. |
| 8,551,167 B2 | 10/2013 | Cuevas |
| 8,556,967 B2 | 10/2013 | Sarfarazi |
| 8,562,674 B2 | 10/2013 | Cole et al. |
| 8,568,478 B2 | 10/2013 | Zickler et al. |
| 8,574,293 B2 | 11/2013 | Kappelhof et al. |
| 8,579,971 B2 | 11/2013 | Webb |
| 8,579,972 B2 | 11/2013 | Rombach |
| 8,585,758 B2 | 11/2013 | Woods |
| 8,585,759 B2 | 11/2013 | Bumbalough |
| 8,608,799 B2 | 12/2013 | Blake |
| 8,608,800 B2 | 12/2013 | Portney |
| 8,613,766 B2 | 12/2013 | Richardson et al. |
| 8,623,082 B2 | 1/2014 | Kappelhof et al. |
| 8,647,384 B2 | 2/2014 | Lu |
| 8,652,206 B2 | 2/2014 | Masket |
| 8,657,877 B2 | 2/2014 | Glazier |
| 8,657,878 B2 | 2/2014 | Mentak et al. |
| 8,900,298 B2 | 12/2014 | Anvar et al. |
| 9,072,600 B2 | 7/2015 | Tran |
| 9,220,590 B2 | 12/2015 | Beer |
| 9,364,318 B2 | 6/2016 | Beer |
| 2001/0001836 A1* | 5/2001 | Cumming .............. A61F 2/1629 623/6.37 |
| 2001/0012964 A1 | 8/2001 | Lang et al. |
| 2001/0016771 A1 | 8/2001 | Cumming |
| 2001/0044657 A1 | 11/2001 | Kellan |
| 2001/0051826 A1 | 12/2001 | Bogaert et al. |
| 2002/0002404 A1 | 1/2002 | Sarfarazi |
| 2002/0013622 A1 | 1/2002 | Hennig |
| 2002/0016630 A1 | 2/2002 | Lang |
| 2002/0045937 A1 | 4/2002 | Sarfarazi |
| 2002/0051063 A1 | 5/2002 | Hwang |
| 2002/0072673 A1 | 6/2002 | Yamamoto et al. |
| 2002/0072795 A1 | 6/2002 | Green |
| 2002/0101564 A1 | 8/2002 | Herrick |
| 2002/0103535 A1 | 8/2002 | Portney |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0116062 A1 | 8/2002 | Portney |
| 2002/0133228 A1 | 9/2002 | Sarver |
| 2002/0138140 A1 | 9/2002 | Hanna |
| 2002/0138141 A1 | 9/2002 | Zadno-Azizi et al. |
| 2002/0143395 A1 | 10/2002 | Skottun |
| 2002/0161435 A1 | 10/2002 | Portney |
| 2002/0173847 A1 | 11/2002 | Pham et al. |
| 2002/0177896 A1 | 11/2002 | Israel |
| 2002/0183843 A1 | 12/2002 | Blake et al. |
| 2002/0193876 A1 | 12/2002 | Lang et al. |
| 2002/0193877 A1 | 12/2002 | Hoffmann et al. |
| 2003/0018386 A1 | 1/2003 | Laguette et al. |
| 2003/0033011 A1 | 2/2003 | Singer et al. |
| 2003/0033013 A1 | 2/2003 | Callahan et al. |
| 2003/0060878 A1 | 3/2003 | Shadduck |
| 2003/0065387 A1 | 4/2003 | Callahan et al. |
| 2003/0074060 A1 | 4/2003 | Zadno-Azizi et al. |
| 2003/0074061 A1 | 4/2003 | Pham et al. |
| 2003/0078655 A1 | 4/2003 | Callahan et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0093149 A1 | 5/2003 | Glazier |
| 2003/0105522 A1 | 6/2003 | Glazier |
| 2003/0109926 A1 | 6/2003 | Portney |
| 2003/0114927 A1 | 6/2003 | Nagamoto |
| 2003/0130732 A1 | 7/2003 | Sarfarazi |
| 2003/0135271 A1 | 7/2003 | Bandhauer |
| 2003/0135273 A1 | 7/2003 | Callahan et al. |
| 2003/0147046 A1 | 8/2003 | Shadduck |
| 2003/0149480 A1 | 8/2003 | Shadduck |
| 2003/0171808 A1 | 9/2003 | Phillips |
| 2003/0171809 A1 | 9/2003 | Phillips |
| 2003/0181977 A1 | 9/2003 | Brady |
| 2003/0187504 A1 | 10/2003 | Weinschenk et al. |
| 2003/0199976 A1 | 10/2003 | Portney |
| 2003/0204254 A1 | 10/2003 | Peng et al. |
| 2003/0204255 A1 | 10/2003 | Peng et al. |
| 2003/0204256 A1 | 10/2003 | Peng et al. |
| 2004/0015236 A1 | 1/2004 | Sarfarazi |
| 2004/0034417 A1 | 2/2004 | Heyman |
| 2004/0064182 A1 | 4/2004 | Kelman |
| 2004/0073304 A1 | 4/2004 | Weinschenk et al. |
| 2004/0082993 A1 | 4/2004 | Woods |
| 2004/0082994 A1 | 4/2004 | Woods et al. |
| 2004/0082995 A1 | 4/2004 | Woods |
| 2004/0100704 A1 | 5/2004 | Shadduck |
| 2004/0106992 A1 | 6/2004 | Lang et al. |
| 2004/0106993 A1 | 6/2004 | Portney |
| 2004/0111152 A1 | 6/2004 | Kelman |
| 2004/0111153 A1 | 6/2004 | Woods et al. |
| 2004/0117013 A1 | 6/2004 | Schachar |
| 2004/0158322 A1 | 8/2004 | Shen |
| 2004/0162612 A1 | 8/2004 | Portney et al. |
| 2004/0169816 A1 | 9/2004 | Esch |
| 2004/0169932 A1 | 9/2004 | Esch et al. |
| 2004/0181279 A1 | 9/2004 | Nun |
| 2004/0184158 A1 | 9/2004 | Shadduck |
| 2004/0190153 A1 | 9/2004 | Esch |
| 2004/0215340 A1 | 10/2004 | Messner et al. |
| 2004/0230300 A1 | 11/2004 | Bandhauer et al. |
| 2004/0236422 A1 | 11/2004 | Zhang et al. |
| 2004/0236423 A1 | 11/2004 | Zhang et al. |
| 2004/0243233 A1 | 12/2004 | Phillips |
| 2004/0249455 A1 | 12/2004 | Tran |
| 2005/0021137 A1 | 1/2005 | Blake et al. |
| 2005/0021138 A1 | 1/2005 | Woods |
| 2005/0021139 A1 | 1/2005 | Shadduck |
| 2005/0049700 A1 | 3/2005 | Zadno-Azizi et al. |
| 2005/0055092 A1 | 3/2005 | Nguyen et al. |
| 2005/0060032 A1 | 3/2005 | Magnante et al. |
| 2005/0071002 A1 | 3/2005 | Glazier |
| 2005/0075732 A1 | 4/2005 | Israel |
| 2005/0085907 A1 | 4/2005 | Hanna |

(56) References Cited

U.S. PATENT DOCUMENTS

| | | |
|---|---|---|
| 2005/0090896 A1 | 4/2005 | Ben Nun |
| 2005/0096498 A1 | 5/2005 | Houser et al. |
| 2005/0096741 A1 | 5/2005 | Cumming |
| 2005/0107873 A1 | 5/2005 | Zhou |
| 2005/0107875 A1 | 5/2005 | Cumming |
| 2005/0113914 A1 | 5/2005 | Miller et al. |
| 2005/0119739 A1 | 6/2005 | Glazier |
| 2005/0119740 A1 | 6/2005 | Esch et al. |
| 2005/0125055 A1 | 6/2005 | Deacon et al. |
| 2005/0125056 A1 | 6/2005 | Deacon et al. |
| 2005/0125057 A1 | 6/2005 | Cumming |
| 2005/0125059 A1* | 6/2005 | Pinchuk .............. A61F 2/1613 623/6.56 |
| 2005/0131535 A1 | 6/2005 | Woods |
| 2005/0137703 A1 | 6/2005 | Chen |
| 2005/0143814 A1 | 6/2005 | Esch et al. |
| 2005/0149183 A1 | 7/2005 | Shadduck |
| 2005/0149184 A1 | 7/2005 | Bogaert |
| 2005/0209692 A1 | 9/2005 | Zhang |
| 2005/0234547 A1 | 10/2005 | Nguyen et al. |
| 2005/0251254 A1 | 11/2005 | Brady et al. |
| 2005/0267575 A1 | 12/2005 | Nguyen et al. |
| 2006/0020339 A1 | 1/2006 | Ran |
| 2006/0030938 A1 | 2/2006 | Altmann |
| 2006/0041307 A1 | 2/2006 | Esch et al. |
| 2006/0047339 A1 | 3/2006 | Brown |
| 2006/0047340 A1 | 3/2006 | Brown |
| 2006/0061729 A1 | 3/2006 | Shadduck |
| 2006/0064162 A1 | 3/2006 | Klima |
| 2006/0069433 A1 | 3/2006 | Nun |
| 2006/0087614 A1 | 4/2006 | Shadduck |
| 2006/0089712 A1 | 4/2006 | Malecaze |
| 2006/0092340 A1 | 5/2006 | Blum et al. |
| 2006/0100701 A1 | 5/2006 | Esch et al. |
| 2006/0100703 A1 | 5/2006 | Evans et al. |
| 2006/0100704 A1 | 5/2006 | Blake et al. |
| 2006/0116765 A1 | 6/2006 | Blake et al. |
| 2006/0142855 A1 | 6/2006 | Vaudant et al. |
| 2006/0149369 A1 | 7/2006 | Cumming et al. |
| 2006/0178741 A1 | 8/2006 | Zadno-Azizi et al. |
| 2006/0178742 A1 | 8/2006 | Nagamoto |
| 2006/0184244 A1 | 8/2006 | Nguyen et al. |
| 2006/0212116 A1 | 9/2006 | Woods |
| 2006/0212117 A1 | 9/2006 | Lang et al. |
| 2006/0247766 A1 | 11/2006 | Marin |
| 2006/0247767 A1 | 11/2006 | Koch |
| 2006/0253196 A1 | 11/2006 | Woods |
| 2006/0259139 A1 | 11/2006 | Zadno-Azizi et al. |
| 2006/0259140 A1 | 11/2006 | Dell |
| 2006/0271186 A1 | 11/2006 | Nishi et al. |
| 2006/0271187 A1 | 11/2006 | Zadno-Azizi et al. |
| 2007/0005135 A1 | 1/2007 | Makker et al. |
| 2007/0005136 A1 | 1/2007 | Richardson |
| 2007/0010880 A1 | 1/2007 | Esch |
| 2007/0010882 A1 | 1/2007 | Barrett |
| 2007/0016293 A1 | 1/2007 | Tran |
| 2007/0021831 A1 | 1/2007 | Clarke |
| 2007/0021832 A1 | 1/2007 | Nordan |
| 2007/0027540 A1 | 2/2007 | Zadno-Azizi et al. |
| 2007/0032866 A1 | 2/2007 | Portney |
| 2007/0050024 A1 | 3/2007 | Zhang |
| 2007/0050025 A1 | 3/2007 | Nguyen et al. |
| 2007/0067030 A1 | 3/2007 | Glazier et al. |
| 2007/0078515 A1 | 4/2007 | Brady |
| 2007/0083260 A1 | 4/2007 | Colvard |
| 2007/0083261 A1 | 4/2007 | Colvard |
| 2007/0088433 A1 | 4/2007 | Esch et al. |
| 2007/0100444 A1 | 5/2007 | Brady et al. |
| 2007/0100445 A1 | 5/2007 | Shadduck |
| 2007/0106377 A1 | 5/2007 | Smith et al. |
| 2007/0106380 A1 | 5/2007 | Terwee et al. |
| 2007/0106381 A1 | 5/2007 | Blake |
| 2007/0108643 A1 | 5/2007 | Zadno-Azizi et al. |
| 2007/0118216 A1 | 5/2007 | Pynson |
| 2007/0123981 A1 | 5/2007 | Tassignon |
| 2007/0129798 A1 | 6/2007 | Chawdhary |
| 2007/0129803 A1 | 6/2007 | Cumming et al. |
| 2007/0135915 A1 | 6/2007 | Klima |
| 2007/0142913 A1 | 6/2007 | Phillips |
| 2007/0156236 A1 | 7/2007 | Stenger |
| 2007/0171366 A1 | 7/2007 | Su et al. |
| 2007/0185574 A1 | 8/2007 | Ben Nun |
| 2007/0203578 A1 | 8/2007 | Scholl et al. |
| 2007/0213817 A1 | 9/2007 | Esch et al. |
| 2007/0239274 A1 | 10/2007 | Kellan |
| 2007/0244560 A1 | 10/2007 | Ossipov et al. |
| 2007/0244561 A1 | 10/2007 | Ben Nun |
| 2007/0260308 A1 | 11/2007 | Tran |
| 2007/0260309 A1 | 11/2007 | Richardson |
| 2007/0260310 A1 | 11/2007 | Richardson |
| 2007/0270946 A1 | 11/2007 | Poley |
| 2007/0299487 A1 | 12/2007 | Shadduck |
| 2008/0004699 A1 | 1/2008 | Ben Nun |
| 2008/0015689 A1 | 1/2008 | Esch et al. |
| 2008/0021549 A1 | 1/2008 | Eagan et al. |
| 2008/0021550 A1 | 1/2008 | Richardson |
| 2008/0033449 A1 | 2/2008 | Cole et al. |
| 2008/0046074 A1 | 2/2008 | Smith et al. |
| 2008/0046075 A1 | 2/2008 | Esch et al. |
| 2008/0046076 A1 | 2/2008 | Rombach |
| 2008/0051801 A1 | 2/2008 | Hovey et al. |
| 2008/0077238 A1 | 3/2008 | Deacon et al. |
| 2008/0077239 A1 | 3/2008 | Zickler et al. |
| 2008/0086206 A1 | 4/2008 | Nasiatka et al. |
| 2008/0086208 A1 | 4/2008 | Nordan |
| 2008/0109077 A1 | 5/2008 | Bos |
| 2008/0109078 A1 | 5/2008 | Rozakis et al. |
| 2008/0154364 A1 | 6/2008 | Richardson et al. |
| 2008/0161913 A1 | 7/2008 | Brady et al. |
| 2008/0161914 A1 | 7/2008 | Brady et al. |
| 2008/0183289 A1 | 7/2008 | Werblin |
| 2008/0188930 A1 | 8/2008 | Mentak et al. |
| 2008/0200982 A1 | 8/2008 | Your |
| 2008/0208335 A1 | 8/2008 | Blum et al. |
| 2008/0215147 A1 | 9/2008 | Werblin |
| 2008/0243247 A1 | 10/2008 | Poley et al. |
| 2008/0269642 A1 | 10/2008 | Deacon et al. |
| 2008/0269882 A1 | 10/2008 | Simpson et al. |
| 2008/0269885 A1 | 10/2008 | Simpson et al. |
| 2008/0269886 A1 | 10/2008 | Simpson et al. |
| 2008/0281417 A1 | 11/2008 | Nagamoto |
| 2008/0300680 A1 | 12/2008 | Joshua |
| 2008/0306587 A1 | 12/2008 | Your |
| 2008/0306588 A1 | 12/2008 | Smiley et al. |
| 2009/0005865 A1 | 1/2009 | Smiley et al. |
| 2009/0005866 A1 | 1/2009 | Cumming |
| 2009/0012609 A1 | 1/2009 | Geraghty et al. |
| 2009/0018652 A1 | 1/2009 | Hermans et al. |
| 2009/0027661 A1 | 1/2009 | Choi et al. |
| 2009/0030425 A1 | 1/2009 | Smiley et al. |
| 2009/0033863 A1 | 2/2009 | Blum et al. |
| 2009/0036982 A1 | 2/2009 | Aharoni et al. |
| 2009/0062912 A1 | 3/2009 | Rombach |
| 2009/0124773 A1 | 5/2009 | Zhou et al. |
| 2009/0125105 A1 | 5/2009 | Lesage et al. |
| 2009/0125106 A1 | 5/2009 | Weinschenk, III et al. |
| 2009/0149952 A1 | 6/2009 | Shadduck |
| 2009/0171458 A1* | 7/2009 | Kellan .............. A61F 2/1629 623/6.46 |
| 2009/0187242 A1 | 7/2009 | Weeber et al. |
| 2009/0198326 A1 | 8/2009 | Zhou et al. |
| 2009/0204209 A1 | 8/2009 | Tran |
| 2009/0204210 A1 | 8/2009 | Pynson |
| 2009/0204211 A1 | 8/2009 | Angelopoulos et al. |
| 2009/0210054 A1 | 8/2009 | Weeber et al. |
| 2009/0228101 A1 | 9/2009 | Zadno-Azizi |
| 2009/0234448 A1 | 9/2009 | Weeber et al. |
| 2009/0234449 A1 | 9/2009 | De Juan, Jr. et al. |
| 2009/0248152 A1 | 10/2009 | Bumbalough |
| 2009/0248154 A1 | 10/2009 | Dell |
| 2009/0264998 A1 | 10/2009 | Mentak et al. |
| 2009/0264999 A1 | 10/2009 | Cumming |
| 2009/0265000 A1 | 10/2009 | Vaudant et al. |
| 2009/0292354 A1 | 11/2009 | Gontijo et al. |

(56) References Cited

U.S. PATENT DOCUMENTS

| | | |
|---|---|---|
| 2009/0292355 A1 | 11/2009 | Boyd et al. |
| 2009/0312836 A1 | 12/2009 | Pinchuk et al. |
| 2009/0319040 A1 | 12/2009 | Khoury |
| 2010/0016964 A1 | 1/2010 | Werblin |
| 2010/0036490 A1 | 2/2010 | Deacon et al. |
| 2010/0094412 A1 | 4/2010 | Wensrich |
| 2010/0094415 A1 | 4/2010 | Bumbalough |
| 2010/0121443 A1 | 5/2010 | Michel et al. |
| 2010/0121444 A1 | 5/2010 | Ben Nun |
| 2010/0131058 A1 | 5/2010 | Shadduck |
| 2010/0131059 A1 | 5/2010 | Callahan et al. |
| 2010/0131061 A1 | 5/2010 | Callahan et al. |
| 2010/0134754 A1 | 6/2010 | Hong et al. |
| 2010/0137983 A1 | 6/2010 | Culbertson et al. |
| 2010/0152848 A1 | 6/2010 | Williamson et al. |
| 2010/0179652 A1 | 7/2010 | Yamamoto et al. |
| 2010/0179653 A1 | 7/2010 | Argento et al. |
| 2010/0198349 A1 | 8/2010 | Brady et al. |
| 2010/0204788 A1 | 8/2010 | Van Noy |
| 2010/0211167 A1 | 8/2010 | Glazier |
| 2010/0211170 A1 | 8/2010 | Liao |
| 2010/0211171 A1 | 8/2010 | Sarfarazi |
| 2010/0228260 A1 | 9/2010 | Callahan et al. |
| 2010/0228344 A1 | 9/2010 | Shadduck |
| 2010/0228346 A1 | 9/2010 | Esch |
| 2010/0292789 A1* | 11/2010 | Willis .................. A61F 2/1602 623/6.11 |
| 2010/0318186 A1 | 12/2010 | Bumbalough et al. |
| 2010/0324671 A1 | 12/2010 | Shadduck |
| 2010/0324672 A1 | 12/2010 | Esch et al. |
| 2010/0324673 A1 | 12/2010 | Nguyen et al. |
| 2011/0029074 A1 | 2/2011 | Reisin et al. |
| 2011/0035001 A1 | 2/2011 | Woods |
| 2011/0035002 A1 | 2/2011 | Nun |
| 2011/0040376 A1 | 2/2011 | Christie et al. |
| 2011/0040378 A1 | 2/2011 | Werblin |
| 2011/0040379 A1 | 2/2011 | Bumbalough |
| 2011/0052020 A1 | 3/2011 | Hildebrand et al. |
| 2011/0054600 A1 | 3/2011 | Bumbalough |
| 2011/0054601 A1 | 3/2011 | Kadziauskas et al. |
| 2011/0071628 A1 | 3/2011 | Gross et al. |
| 2011/0082544 A1 | 4/2011 | Ben Nun |
| 2011/0093067 A1 | 4/2011 | Michalek et al. |
| 2011/0098810 A1 | 4/2011 | Altmann |
| 2011/0098812 A1 | 4/2011 | Ben Nun |
| 2011/0112635 A1 | 5/2011 | Ben Nun |
| 2011/0112636 A1 | 5/2011 | Ben Nun |
| 2011/0112638 A1 | 5/2011 | Hermans et al. |
| 2011/0118836 A1 | 5/2011 | Jain et al. |
| 2011/0153014 A1 | 6/2011 | Zhang et al. |
| 2011/0153015 A1 | 6/2011 | Simonov et al. |
| 2011/0160852 A1 | 6/2011 | Mentak et al. |
| 2011/0184514 A1 | 7/2011 | Angelopoulos et al. |
| 2011/0191086 A1 | 8/2011 | Callahan et al. |
| 2011/0224788 A1 | 9/2011 | Webb |
| 2011/0238174 A1 | 9/2011 | Hong et al. |
| 2011/0245920 A1 | 10/2011 | Richardson |
| 2011/0251686 A1 | 10/2011 | Masket |
| 2011/0257742 A1 | 10/2011 | Bumbalough et al. |
| 2011/0270389 A1 | 11/2011 | Glazer et al. |
| 2011/0282441 A1 | 11/2011 | Zadno-Azizi |
| 2011/0282442 A1 | 11/2011 | Scholl et al. |
| 2011/0282443 A1 | 11/2011 | Smiley et al. |
| 2011/0288638 A1 | 11/2011 | Smiley et al. |
| 2011/0295368 A1 | 12/2011 | Betser |
| 2011/0304058 A1 | 12/2011 | Pendse |
| 2011/0307058 A1 | 12/2011 | Beer |
| 2011/0313522 A1 | 12/2011 | Hayes |
| 2011/0313523 A1 | 12/2011 | Hayes |
| 2012/0010704 A1 | 1/2012 | Bumbalough |
| 2012/0016473 A1 | 1/2012 | Brady et al. |
| 2012/0022547 A1 | 1/2012 | Hildebrand et al. |
| 2012/0029632 A1 | 2/2012 | Ben Nun |
| 2012/0035724 A1 | 2/2012 | Clarke |
| 2012/0046743 A1 | 2/2012 | Pinchuk |
| 2012/0046744 A1 | 2/2012 | Woods et al. |
| 2012/0059465 A1 | 3/2012 | Brady et al. |
| 2012/0078361 A1 | 3/2012 | Shadduck |
| 2012/0078363 A1 | 3/2012 | Lu |
| 2012/0078364 A1 | 3/2012 | Stenger |
| 2012/0116506 A1 | 5/2012 | Compertore |
| 2012/0130487 A1 | 5/2012 | Doraiswamy et al. |
| 2012/0130488 A1 | 5/2012 | Doraiswamy et al. |
| 2012/0143327 A1 | 6/2012 | Bumbalough |
| 2012/0150292 A1 | 6/2012 | Mentak et al. |
| 2012/0203338 A1 | 8/2012 | Jain |
| 2012/0232648 A1 | 9/2012 | Kahook et al. |
| 2012/0232650 A1 | 9/2012 | Hermans et al. |
| 2012/0232651 A1 | 9/2012 | Kahook et al. |
| 2012/0245591 A1 | 9/2012 | Matthews |
| 2012/0245684 A1 | 9/2012 | Liao |
| 2012/0253458 A1 | 10/2012 | Geraghty et al. |
| 2012/0253459 A1 | 10/2012 | Reich et al. |
| 2012/0290084 A1 | 11/2012 | Coroneo |
| 2012/0296425 A1 | 11/2012 | Cumming |
| 2012/0296426 A1 | 11/2012 | Brady et al. |
| 2012/0303119 A1 | 11/2012 | Callahan et al. |
| 2012/0310338 A1 | 12/2012 | Christie et al. |
| 2012/0310342 A1 | 12/2012 | Nguyen et al. |
| 2012/0310343 A1 | 12/2012 | Van Noy |
| 2012/0310344 A1 | 12/2012 | Cumming |
| 2012/0310345 A1 | 12/2012 | Olcina Portilla |
| 2012/0323320 A1 | 12/2012 | Simonov et al. |
| 2012/0323321 A1 | 12/2012 | Simonov et al. |
| 2012/0330415 A1 | 12/2012 | Callahan et al. |
| 2013/0013060 A1 | 1/2013 | Zadno-Azizi et al. |
| 2013/0018461 A1 | 1/2013 | Ben Nun |
| 2013/0030525 A1 | 1/2013 | Brady et al. |
| 2013/0035760 A1 | 2/2013 | Portney |
| 2013/0053954 A1 | 2/2013 | Rao et al. |
| 2013/0060330 A1 | 3/2013 | Weeber et al. |
| 2013/0060331 A1 | 3/2013 | Shadduck |
| 2013/0060332 A1 | 3/2013 | Simpson |
| 2013/0073039 A1 | 3/2013 | Mirlay |
| 2013/0103146 A1 | 4/2013 | Smiley et al. |
| 2013/0103147 A1 | 4/2013 | Christie et al. |
| 2013/0110235 A1 | 5/2013 | Schwiegerling |
| 2013/0116781 A1 | 5/2013 | Ben Nun |
| 2013/0131794 A1 | 5/2013 | Smiley et al. |
| 2013/0138208 A1 | 5/2013 | Simonov et al. |
| 2013/0150961 A1 | 6/2013 | Evans et al. |
| 2013/0166026 A1 | 6/2013 | Bumbalough |
| 2013/0184816 A1 | 7/2013 | Hayes |
| 2013/0190868 A1 | 7/2013 | Kahook et al. |
| 2013/0197635 A1 | 8/2013 | Phillips |
| 2013/0204364 A1 | 8/2013 | Olson |
| 2013/0204365 A1 | 8/2013 | Dell |
| 2013/0226294 A1 | 8/2013 | Van Der Mooren et al. |
| 2013/0226295 A1 | 8/2013 | de Juan, Jr. et al. |
| 2013/0231741 A1 | 9/2013 | Clarke |
| 2013/0231742 A1 | 9/2013 | Deacon et al. |
| 2013/0238091 A1 | 9/2013 | Danta et al. |
| 2013/0245754 A1 | 9/2013 | Blum et al. |
| 2013/0245756 A1 | 9/2013 | Liao |
| 2013/0250239 A1 | 9/2013 | Hildebrand et al. |
| 2013/0268070 A1 | 10/2013 | Esch et al. |
| 2013/0268071 A1 | 10/2013 | Vilupuru et al. |
| 2013/0282117 A1 | 10/2013 | Van Heugten et al. |
| 2013/0297018 A1 | 11/2013 | Brady et al. |
| 2013/0304202 A1 | 11/2013 | Basinger |
| 2013/0304203 A1 | 11/2013 | Berr |
| 2013/0304204 A1 | 11/2013 | Bumbalough et al. |
| 2013/0310931 A1 | 11/2013 | Kahook et al. |
| 2013/0310932 A1 | 11/2013 | Kellan |
| 2013/0317606 A1 | 11/2013 | Culbertson et al. |
| 2013/0317608 A1 | 11/2013 | Hermans et al. |
| 2013/0331937 A1 | 12/2013 | Stevens |
| 2013/0338767 A1 | 12/2013 | Mazzocchi et al. |
| 2013/0345713 A1 | 12/2013 | Cole et al. |
| 2014/0005780 A1 | 1/2014 | Zhao |
| 2014/0005781 A1 | 1/2014 | Zhao et al. |
| 2014/0005782 A1 | 1/2014 | Kellan et al. |
| 2014/0012277 A1 | 1/2014 | Matthews et al. |
| 2014/0052245 A1 | 2/2014 | Zickler et al. |

(56) References Cited

U.S. PATENT DOCUMENTS

| | | |
|---|---|---|
| 2014/0052246 A1 | 2/2014 | Kahook et al. |
| 2014/0058507 A1 | 2/2014 | Reich et al. |
| 2014/0142588 A1 | 5/2014 | Hildebrand et al. |
| 2014/0180403 A1 | 6/2014 | Silvestrini et al. |
| 2014/0180405 A1 | 6/2014 | Weinschenk, III et al. |
| 2014/0180406 A1 | 6/2014 | Simpson |
| 2014/0180407 A1 | 6/2014 | Sohn et al. |
| 2014/0194859 A1 | 7/2014 | Ianchulev |
| 2014/0249625 A1 | 9/2014 | Shadduck |
| 2015/0087743 A1 | 3/2015 | Anvar et al. |
| 2015/0088254 A1 | 3/2015 | Cumming |
| 2015/0105760 A1 | 4/2015 | Rao et al. |
| 2015/0134059 A1 | 5/2015 | Curatu |
| 2015/0142108 A1 | 5/2015 | Akura et al. |
| 2015/0202041 A1 | 7/2015 | Shadduck |
| 2015/0238310 A1 | 8/2015 | Matthews et al. |
| 2015/0257874 A1 | 9/2015 | Hildebrand et al. |
| 2016/0030161 A1 | 2/2016 | Brady et al. |
| 2016/0038278 A1 | 2/2016 | Matthews |
| 2016/0128826 A1 | 5/2016 | Silvestrini et al. |
| 2016/0157996 A1 | 6/2016 | Dolla et al. |
| 2016/0184091 A1 | 6/2016 | Smiley et al. |
| 2016/0184092 A1 | 6/2016 | Smiley et al. |
| 2016/0262875 A1 | 9/2016 | Smith et al. |
| 2016/0317286 A1 | 11/2016 | Brady et al. |
| 2016/0317287 A1 | 11/2016 | Silvestrini et al. |
| 2016/0361157 A1 | 12/2016 | Honigsbaum |
| 2017/0020662 A1 | 1/2017 | Shadduck |
| 2017/0049561 A1 | 2/2017 | Smiley et al. |

FOREIGN PATENT DOCUMENTS

| | | |
|---|---|---|
| AU | 2003300879 A1 | 7/2004 |
| AU | 2004211746 A1 | 8/2004 |
| AU | 2004219674 A1 | 9/2004 |
| AU | 2005299661 A1 | 5/2006 |
| AU | 2006265668 A1 | 1/2007 |
| AU | 2006304339 A1 | 4/2007 |
| AU | 2007340043 A1 | 7/2008 |
| AU | 2008218313 A1 | 8/2008 |
| AU | 2008279167 A1 | 1/2009 |
| AU | 2008279173 A1 | 1/2009 |
| AU | 2010235988 A1 | 11/2010 |
| AU | 2010203427 A1 | 7/2011 |
| AU | 2012335677 A1 | 5/2014 |
| AU | 2014202532 A1 | 7/2014 |
| AU | 2013235467 A1 | 9/2014 |
| AU | 2015258287 A1 | 12/2015 |
| AU | 2017216460 A1 | 8/2017 |
| AU | 2016275073 A1 | 1/2018 |
| AU | 2018200978 A1 | 3/2018 |
| AU | 2016349532 A1 | 4/2018 |
| AU | 2019201556 A1 | 3/2019 |
| CA | 2506753 A1 | 6/2004 |
| CA | 2508143 A1 | 6/2004 |
| CA | 2507694 A1 | 7/2004 |
| CA | 2515355 A1 | 8/2004 |
| CA | 2584472 A1 | 5/2006 |
| CA | 2613580 A1 | 1/2007 |
| CA | 2626269 A1 | 4/2007 |
| CA | 2674816 A1 | 7/2008 |
| CA | 2676713 A1 | 8/2008 |
| CA | 2693906 A1 | 1/2009 |
| CA | 2696450 A1 | 1/2009 |
| CA | 2748812 A1 | 7/2010 |
| CA | 2854919 A1 | 5/2013 |
| CA | 2865954 A1 | 9/2013 |
| CA | 2987311 A1 | 12/2016 |
| CA | 3001477 A1 | 5/2017 |
| DE | 112010004191 T5 | 11/2012 |
| EP | 1563337 A2 | 8/2005 |
| EP | 1569581 A1 | 9/2005 |
| EP | 1585563 A2 | 10/2005 |
| EP | 1590702 A2 | 11/2005 |
| EP | 1599748 A2 | 11/2005 |
| EP | 1816984 A2 | 8/2007 |
| EP | 1906882 A2 | 4/2008 |
| EP | 1948084 A2 | 7/2008 |
| EP | 2053991 A2 | 5/2009 |
| EP | 2094193 A2 | 9/2009 |
| EP | 2112932 A2 | 11/2009 |
| EP | 2178462 A2 | 4/2010 |
| EP | 2178463 A2 | 4/2010 |
| EP | 2178464 A2 | 4/2010 |
| EP | 2221024 A1 | 8/2010 |
| EP | 2384167 A2 | 11/2011 |
| EP | 2473138 A2 | 7/2012 |
| EP | 2539351 A2 | 1/2013 |
| EP | 2559405 A2 | 2/2013 |
| EP | 2563275 A1 | 3/2013 |
| EP | 2647353 A1 | 10/2013 |
| EP | 2671541 A1 | 12/2013 |
| EP | 2688515 A2 | 1/2014 |
| EP | 2775961 A1 | 9/2014 |
| EP | 2827804 A1 | 1/2015 |
| EP | 2934383 A1 | 10/2015 |
| EP | 2967842 A1 | 1/2016 |
| EP | 3049023 A1 | 8/2016 |
| EP | 3062741 A1 | 9/2016 |
| EP | 3062742 A1 | 9/2016 |
| EP | 3174500 A1 | 6/2017 |
| EP | 3181094 A1 | 6/2017 |
| EP | 3197462 A1 | 8/2017 |
| EP | 3263574 A1 | 1/2018 |
| EP | 3307206 A1 | 4/2018 |
| EP | 3370647 A1 | 9/2018 |
| EP | 3383320 A1 | 10/2018 |
| GB | 1583193 A | 1/1981 |
| HK | 1227277 A | 10/2017 |
| HK | 1227679 A | 10/2017 |
| HK | 1234303 A | 2/2018 |
| HK | 1235658 A | 3/2018 |
| HK | 1239501 A | 5/2018 |
| HK | 1241712 A | 6/2018 |
| HK | 1242207 A | 6/2018 |
| IN | 6305DELNP2015 A | 7/2016 |
| IN | 201617018083 A | 8/2016 |
| IN | 201717013927 A | 8/2017 |
| IN | 201617044673 A | 2/2018 |
| JP | 2014061387 A | 4/2014 |
| NL | 2012420 A | 9/2014 |
| WO | WO 2001017461 | 3/2001 |
| WO | WO-2004046768 A2 | 6/2004 |
| WO | WO-2004052242 A1 | 6/2004 |
| WO | WO-2004054471 A2 | 7/2004 |
| WO | WO-2004072689 A2 | 8/2004 |
| WO | WO-2006047383 A2 | 5/2006 |
| WO | WO-2007005778 A2 | 1/2007 |
| WO | WO-2007047529 A2 | 4/2007 |
| WO | WO-2007047530 A2 | 4/2007 |
| WO | WO-2008024766 A2 | 2/2008 |
| WO | WO-2008077040 A2 | 6/2008 |
| WO | WO-2008082957 A2 | 7/2008 |
| WO | WO-2008103798 A2 | 8/2008 |
| WO | WO-2009015161 A2 | 1/2009 |
| WO | WO-2009015226 A2 | 1/2009 |
| WO | WO-2009015234 A2 | 1/2009 |
| WO | WO-2009015240 A2 | 1/2009 |
| WO | WO-2010081093 A2 | 7/2010 |
| WO | WO-2011026068 A2 | 3/2011 |
| WO | WO-2011106435 A2 | 9/2011 |
| WO | WO-2011137191 A1 | 11/2011 |
| WO | WO-2012006616 A2 | 1/2012 |
| WO | WO-20120106673 A1 | 8/2012 |
| WO | WO-2012129407 A2 | 9/2012 |
| WO | WO-2013070924 A1 | 5/2013 |
| WO | WO-2013142323 A1 | 9/2013 |
| WO | WO-2013166068 A1 | 11/2013 |
| WO | WO-2014099630 A1 | 6/2014 |
| WO | WO-2014134302 A1 | 9/2014 |
| WO | WO-2014145562 A1 | 9/2014 |
| WO | WO-2015148673 A1 | 10/2015 |
| WO | WO-2016018932 A1 | 2/2016 |
| WO | WO-2016049059 A1 | 3/2016 |

(56) References Cited

FOREIGN PATENT DOCUMENTS

| WO | WO-2016201351 A1 | 12/2016 |
| WO | WO-2017079733 A1 | 5/2017 |
| WO | WO-2017085344 A1 | 5/2017 |

OTHER PUBLICATIONS

U.S. Appl. No. 13/800,367, filed Mar. 13, 2013 by Paul Marius Beer.
Non-Final Office Action in U.S. Appl. No. 13/800,367 dated Oct. 21, 2014.
Final Office Action in U.S. Appl. No. 13/800,367 dated May 14, 2015.
International Search Report and Written Opinion in PCT/US2017/048219 dated Jan. 2, 2018, 19 pages.
Communication Pursuant to Article 94(3) EPC dated Oct. 11, 2018 in European Patent Application No. 13725509.7, 9 pages.
Communication Pursued to Article 94(3) EPC dated May 9, 2018 in European Patent Application No. 13725509.7, 3 pages.
Communication Pursued to Article 94(3) EPC dated Oct. 11, 2018 in European Patent Application No. 13725509.7, 9 pages.
Communication Pursued to Rule 161(1) and 162 EPC dated Apr. 2, 2019 in European Patent Application No. 17772509.0, 3 pages.

\* cited by examiner

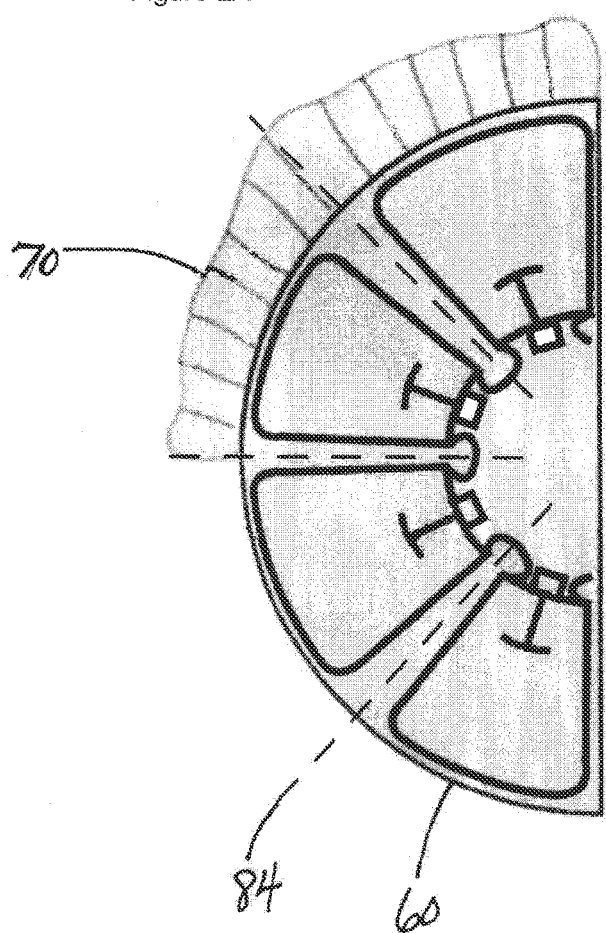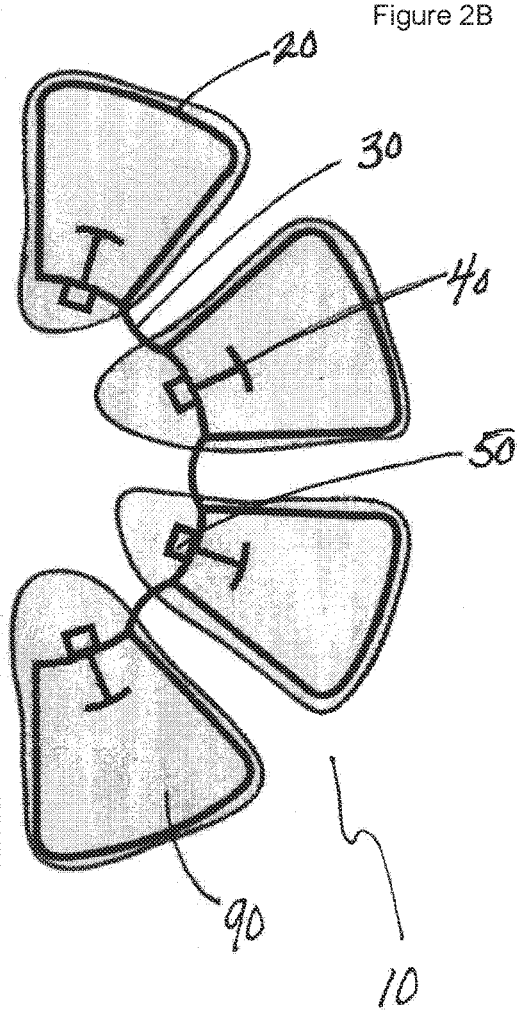

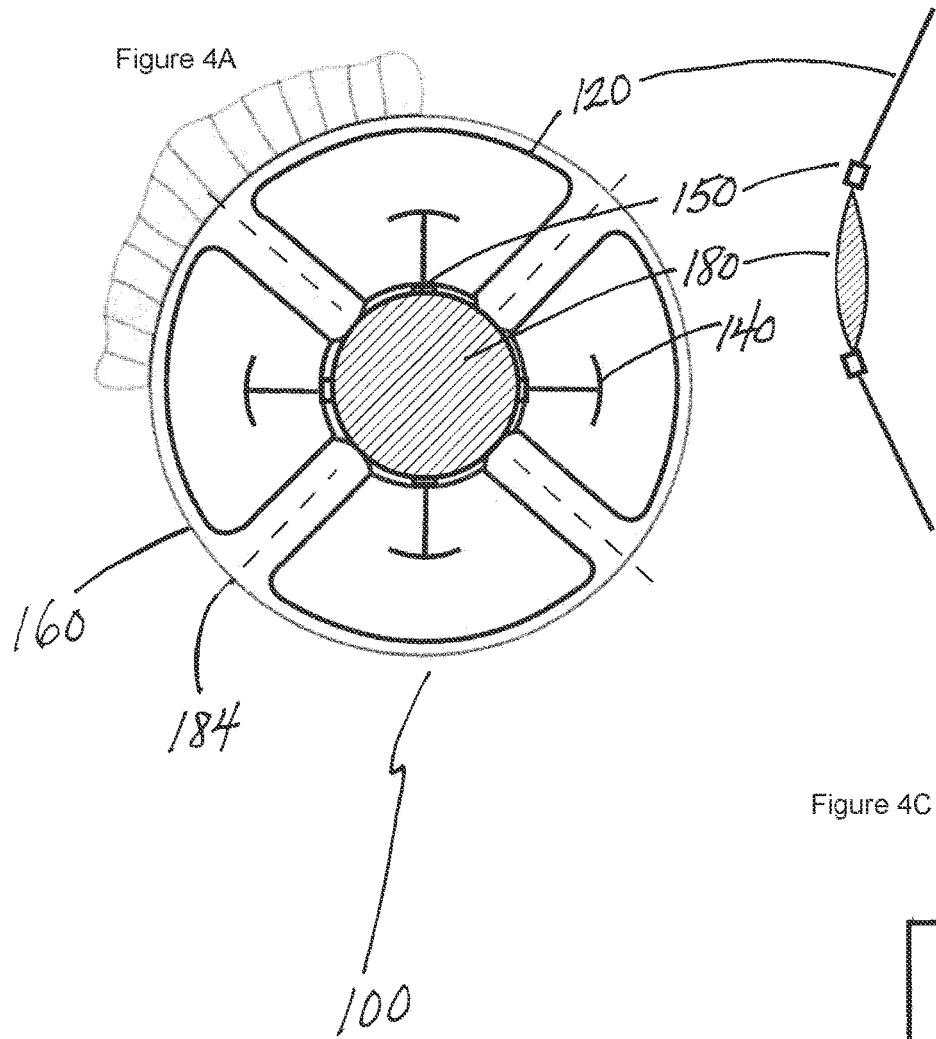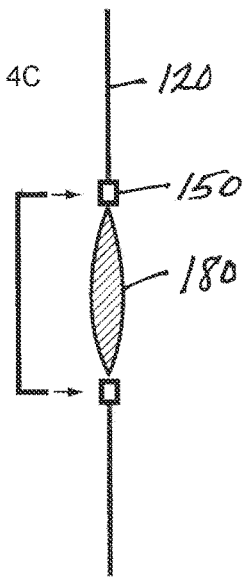

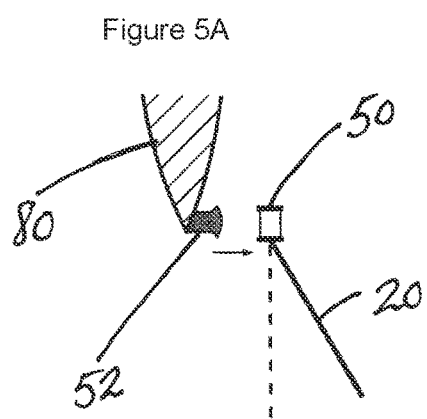
Figure 5A
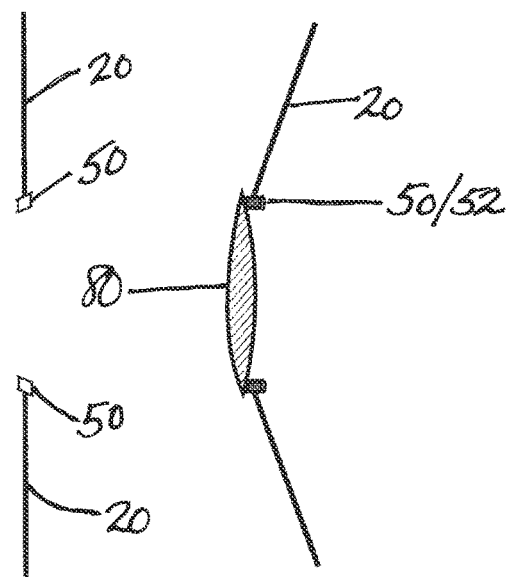
Figure 5B
Figure 5C
FIGURE 5

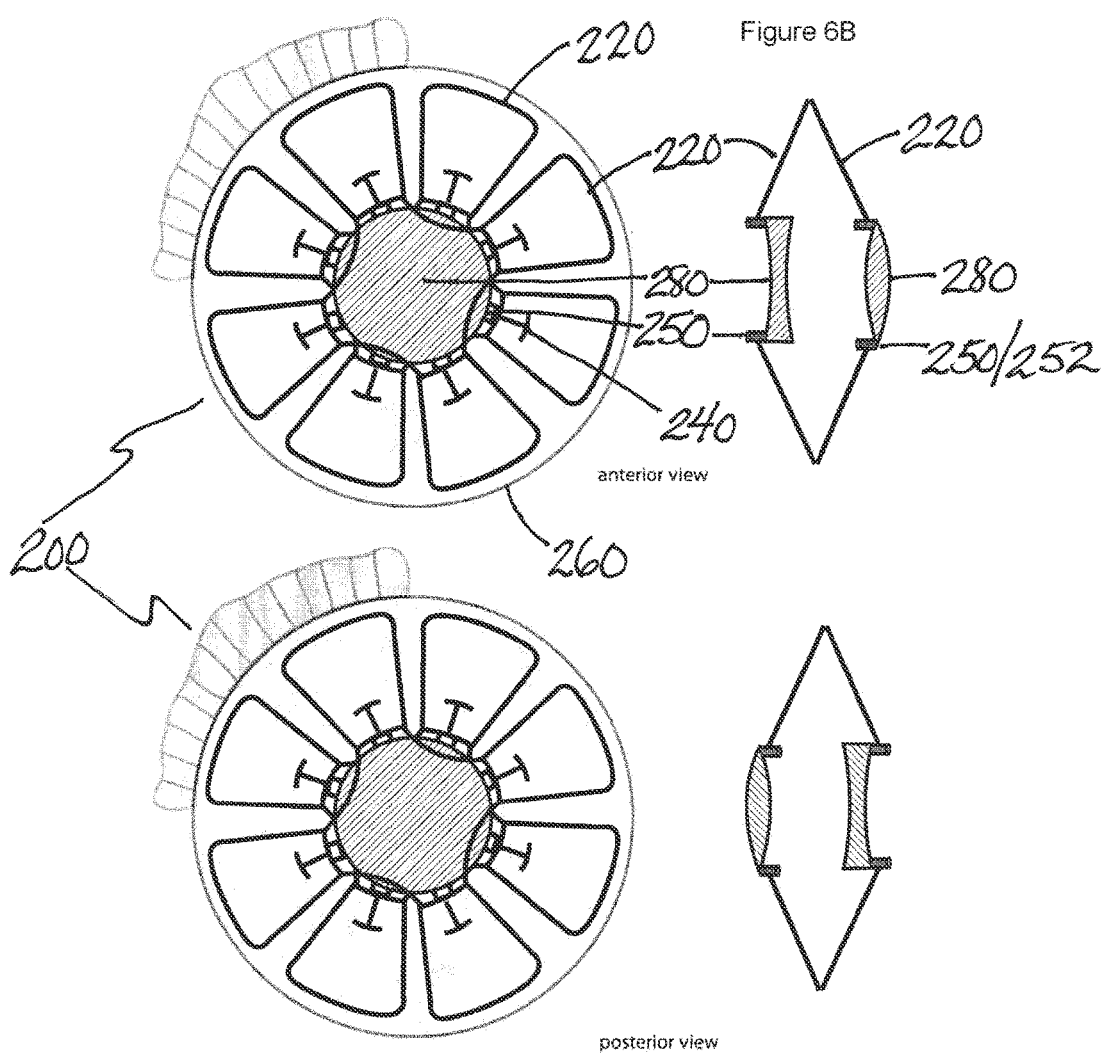

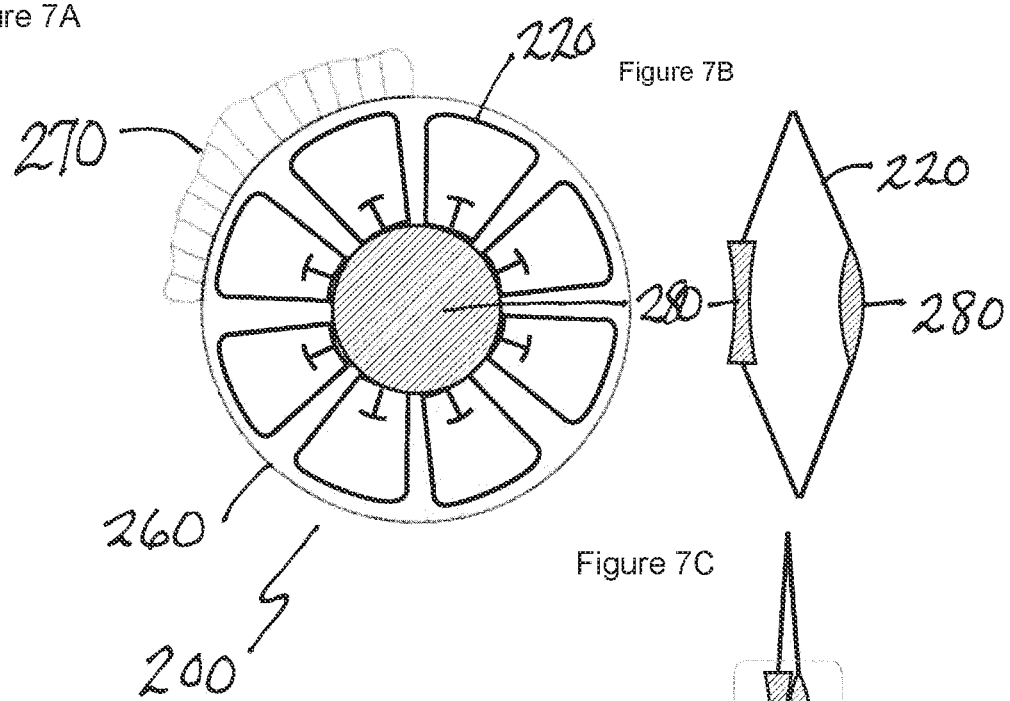
Figure 7A
Figure 7B
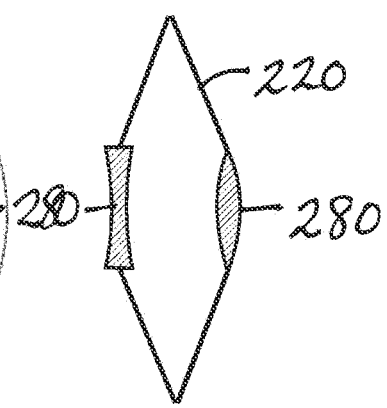
Figure 7C
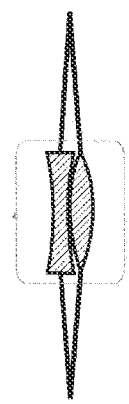

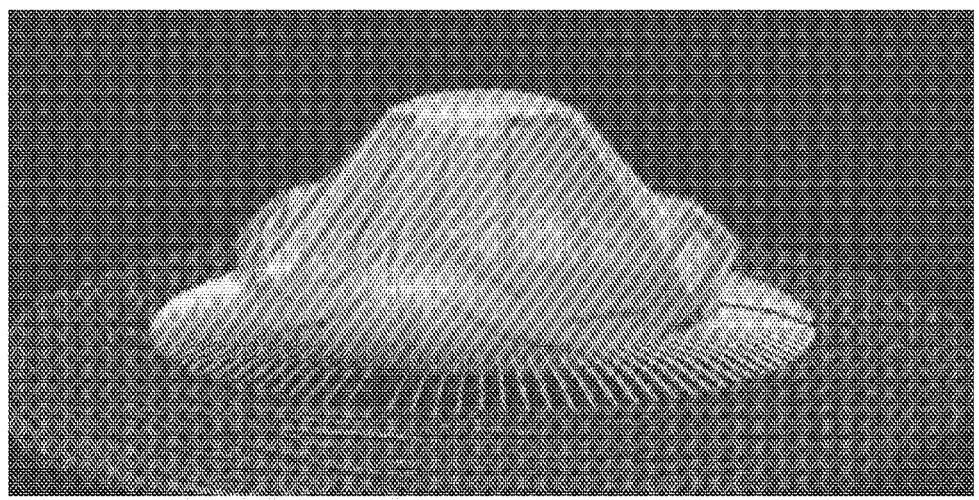
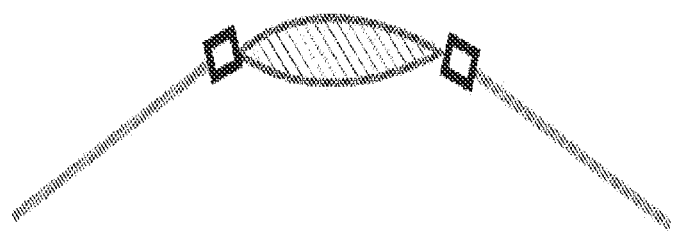
Figure 11

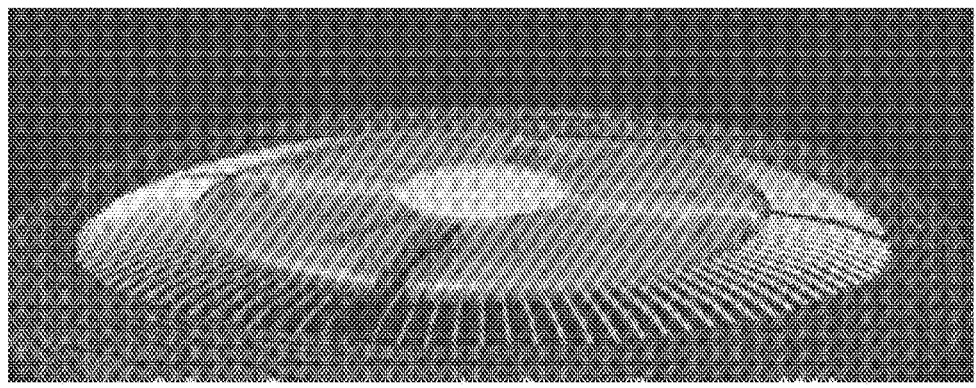
Figure 12

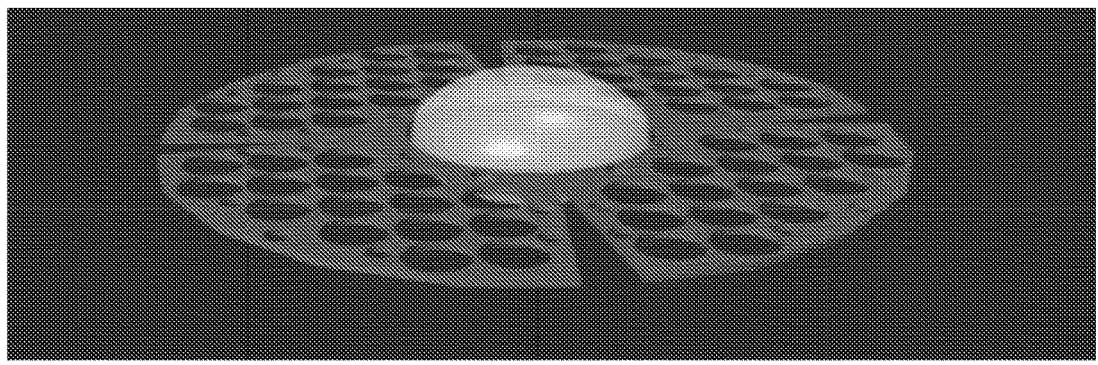
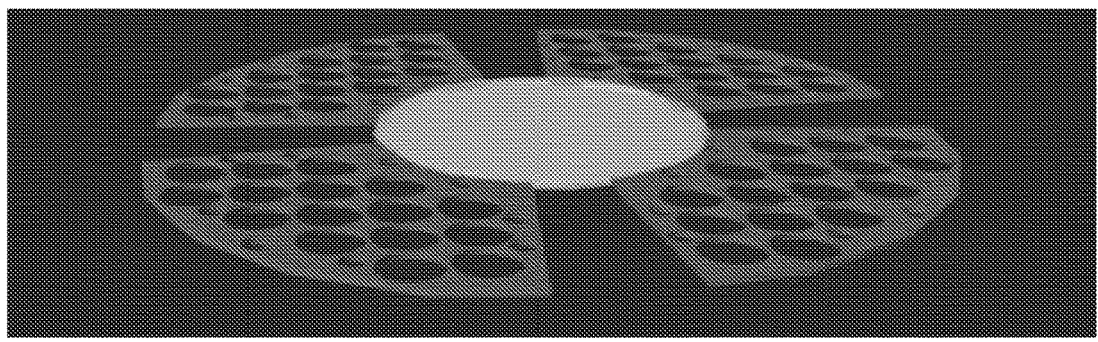
Figure 13

ACCOMMODATIVE INTRAOCULAR LENS AND METHOD OF IMPROVING ACCOMMODATION

CROSS REFERENCE TO RELATED APPLICATIONS

The present application is a divisional of U.S. patent application Ser. No. 13/157,703, filed Jun. 10, 2011, which claims the priority of U.S. provisional application No. 61/353,273, filed Jun. 10, 2010 and U.S. provisional application No. 61/368,862, filed Jul. 29, 2010. The contents of those applications are hereby incorporated by reference into the present disclosure in their entirety.

TECHNICAL FIELD

The present invention relates generally to intraocular lenses. More particularly, the present invention relates to accommodative, intraocular lens systems and methods for improving accommodation.

BACKGROUND INFORMATION

Under normal conditions, a healthy human eye focuses on near and distant objects by contraction and relaxation of the ciliary muscle thereby contracting and releasing the tension on the zonules in the eye. The contraction of the ciliary muscle releases zonular tension (accomodative state) and allows the lens to alter to a more globular or spherical resting shape. The relaxation of the ciliary muscle increases tension on zonules and elastic forces in the eye tissue overcome the inherent lens elasticity and result in stretching the lens equator and flattening the lens curvature (un-accomodative state).

In certain instances, for example when age-related opacification of the lens (cataract) interferes with vision, the natural crystalline lens of the eye needs to be removed. Generally, the natural lens is replaced with an artificial one, for example, an intraocular lens (IOL). Unfortunately, conventional IOLs, even those that profess to be accommodative, may be unable to provide sufficient spatial displacement of the lens along the optical axis to provide an adequate amount of accommodation for near vision.

In conventional extracapsular cataract surgery, the crystalline lens matrix is removed by phacoemulsification through a curvilinear capsularhexis leaving intact the thin walls of the anterior and posterior capsules, together with zonular ligament connections to the ciliary body and ciliary muscles. An intraocular lens is then placed in the capsular bag, which collapses around the IOL.

Conventional single-optic accommodative intraocular lenses (AIOL) rely on the interaction of the ciliary muscle with the zonule and capsule to induce movement of the optic of the AIOL along its optical axis. Typically, the AIOL is secured within the capsular bag by two or more haptics that translate the radial stretching force exerted on the capsular bag by the zonules in an attempt to achieve the desired axial displacement of the optic.

However, during the post-implantation fibrotic healing process, the anterior capsule fuses with the posterior capsule to form a rigid capsular disc. Loss of elasticity of the capsular disc results and constrains the amount of movement that can be generated by the zonular force or elastic recoil of the intraocular lens and therefore, leads to a decrease in the amount of axial displacement of the lens that can be achieved.

Various lens systems have been designed to address this loss of accommodation. Passive-shift single-optic lenses, the only accommodative lens currently marketed, were designed to move forward under ciliary muscle contraction. Accommodation in these systems, however, remains limited by the loss of elasticity in the post-fibrotic capsule. Even the limited amount of accomodative amplitudes generated by these lenses immediately after surgery is lost within the first few weeks or month after surgery as capsular fibrosis ensures.

Accommodative lens designs with single or multiple optic lens assemblies have been disclosed, for example, in U.S. Pat. Nos. and U.S. application nos. 2009/0125106, 2005/0209692, 2007/0156236, 2009/0005866, 2007/0005136, 2009/0248154. Dual optic lenses retain the problem of capsular fibrosis and loss of amplitude/movement even though they are reported to provide a significant amount of accommodation. However, concerns about possible long-term formation of interlenticular opacification remain.

More recently, a lens systems that employs an active-shift mechanism using repulsive mini-magnets as a means of making accommodation partially independent of the zonules and mechanical properties of the capsular bag was disclosed (see U.S. Pat. Application Nos. 2009/0204210 and 2007/0118216. Still other methods of achieving accommodation include introduction of a polymerizable fluid with a desired refractive index into the capsular bag (lens refilling). Extensive investigation into the feasibility of these methods is still needed.

U.S. Publication No. 2009/0234449 discloses an intraocular lens comprising an accommodating element that is in contact with a substantial portion of the zonular region; the accommodating element is positioned relative to optical element and configured to cooperate with the ciliary muscle, the zonules and/or the vitreous pressure in the eye to effect a shape change to the optical element. According to the '449 publication, prior art multiple lens systems can be cumbersome and also require an axial displacement unachievable with a collapsed capsular bag and resulting ineffective accommodative mechanisms.

The need remains therefore, for an intraocular lens system and an effective mechanism for improving the accommodative capacity of an IOL following implantation. None of the current lens concepts take into account that the devitalized capsular bag after cataract surgery changes its physical properties from an elastic sphere to a contracted rigid disc.

SUMMARY OF THE INVENTION

Briefly, the present invention provides an intraocular lens system and method for improving accommodation that remedies the loss of axial and centrifugal movement caused by shrinkage and loss of flexibility of the capsular bag following implantation of conventional lens systems. A lens system of the present invention includes a flexible optic holder comprising a plurality of zonular capture haptics, in particular, regularly-spaced haptics that are adapted to allow or facilitate fusion of the capsular bag following placement of the optic holder within the capsular bag and ultimately to permit the sectioning of the fused capsular disc. During fusion, each haptic becomes permanently entrapped in its respective capsular disc section; sectioning frees adjacent haptics from each other; each haptic can, therefore, move independently in response to ciliary muscle and zonular forces on the capsule. The action of the zonular capture haptics can be translated to different types of optics suited to provide accomodative amplitude. The restored elasticity of the present accomodative IOL system, which allows the optic to return to a resting state when zonular tension is released, is provided by angulated haptics which straighten under zonular tension, by the elasticity of the optic or a combination of both.

The novel optic holder of the invention is implanted in two stages: first, the optic holder (which may or may not include an integral optic at this stage) is implanted and sufficient time is allowed for fusion of the anterior and posterior leaves of the capsular bag around the implanted device. In a second stage, the fused and fibrosed capsular bag is sectioned at regular intervals determined by spaces between the haptics of the optic holder, to reduce its rigidity, thereby restoring some of the movement lost during fusion of the capsule, fibrosis and formation of the capsular disc. The force of the zonules is uniformly transmitted to the lens via the entrapped haptics.

Unless it is already an integral part of the zonular capture haptic, the optic of the lens system may be inserted into the haptic during a second stage of the procedure. Any mechanical means or chemically-induced tensioning or positioning of the haptic/optic complex, which may have been employed to control the accomodative state of the haptic-lens complex during the fusion and contraction of the healing capsular bag would be removed at this juncture.

In one aspect, therefore, the present invention relates to a method for improving accommodation with an intraocular lens (IOL) system, the method comprising introducing a flexible optic holder with zonular capture haptics into the capsular bag of an eye of a subject and allowing a period of time sufficient for fibrosis of the capsule to occur so that the zonular capture haptics are captured within the fused capsule. During this time the eye may be maintained in either an unaccommodative or accommodative state by administration of an agent to inhibit or induce accommodation, for example, atropine or pilocarpine, respectively. Alternatively, mechanical means may be used to retain the capsule in a flattened and maximally (unaccommodated) or minimally (accommodated) expanded configuration. Apposition of the anterior and posterior leaves of the capsule to facilitate fusion may also be achieved by introduction of an air bubble anterior to the capsular bag. Other mechanical, chemical or biological means may be utilized to enhance the adhesion of the anterior and posterior capsule.

In a second stage, cuts are made in the fibrotic capsular disc at sectioning intervals between the zonular capture haptics of the optic holder. In some embodiments, during this second procedure, the optic is inserted into the holder.

In a related aspect, the invention relates to a flexible optic holder comprising an arrangement of zonular capture haptics that permits 1) complete integration of the haptics during fusion of the capsule to form a capsular disc and 2) sectioning of the fused capsular disc. The optic holder comprises a plurality of hollow closed-loop or fenestrated haptics that extend outwardly from the center of the optic holder to define a disc that is roughly coextensive with the capsular disc and provides a template for sectioning of the disc following fusion. The optic holder of the invention is configured to provide support for an optic, to facilitate fusion and fibrosis of the capsular disc, to allow sectioning of the fused capsular disc and to uniformly translate force from the zonules to the optic.

In one aspect, the invention relates to an intraocular lens system for implantation in a capsular bag of an eye, comprising 1) a flexible optic holder comprising a plurality of haptics that extend outwardly from the center of the optic holder with sectioning regions therebetween where the haptics define a disc that is roughly coextensive with the capsular disc; and 2) an optic adapted to fit into the optic holder. The intraocular lens system is configured to be coextensive with the capsular bag when placed therein and to become fixed within the capsular bag once fusion of the capsular bag has occurred.

The optic holder comprises a plurality of regularly spaced haptics, for example, from 3 to 120 haptics. In an alternate embodiment, the flexible optic holder comprises a single haptic with a fenestrated structure or of a surgical mesh or similar woven material with holes sufficiently large to allow contact and fusion of the anterior and posterior capsule through the fenestrae or holes. The haptics are spaced at regular intervals, with the space between adjacent members defining a sectioning region.

These and other objects, features and advantages of this invention will become apparent from the following detailed description of the various aspects of the invention taken in conjunction with the accompanying drawings.

BRIEF DESCRIPTION OF THE DRAWINGS

FIG. 1b shows the optic holder in its expanded form.

FIGS. 2a and 2b show one embodiment of the invention inside the capsule of an eye prior to (2a) and following sectioning of the capsular bag (2b).

FIG. 4a shows an alternate embodiment of the optic holder in the capsule, prior to sectioning, in which an optic has been secured. FIG. 4b shows the position of the haptics relative to the optic during accommodation; FIG. 4c shows the relative positions of the haptics and the optic under zonular tension (un-accomodative state). A staple-like retainer, for stabilizing the optic during fusion is also shown.

FIG. 5a shows an embodiment in which a snap-like fastener is used as optic attachment means for securing optic in optic holder; 5b shows the relative positions of the haptics and optic attachment means when the optic holder is fused within the capsule; 5c shows the relative positions of the haptics and optic during accommodation following sectioning of the capsular disc.

FIG. 6a shows anterior and posterior views of a dual-optic system in which two optic holders (black and gray) are used; FIG. 6b shows the position of the two optics during accommodation.

FIG. 7a shows an embodiment of the dual-optic system in which optics are an integral part of the optic holders; the positions of the two optics during accommodation (7b), and unaccommodation (7c) are shown.

in the absence of zonular tension (accommodation), the optic is more spherical (9b) than when it is in the unaccommodated state (9c).

Figure 10:
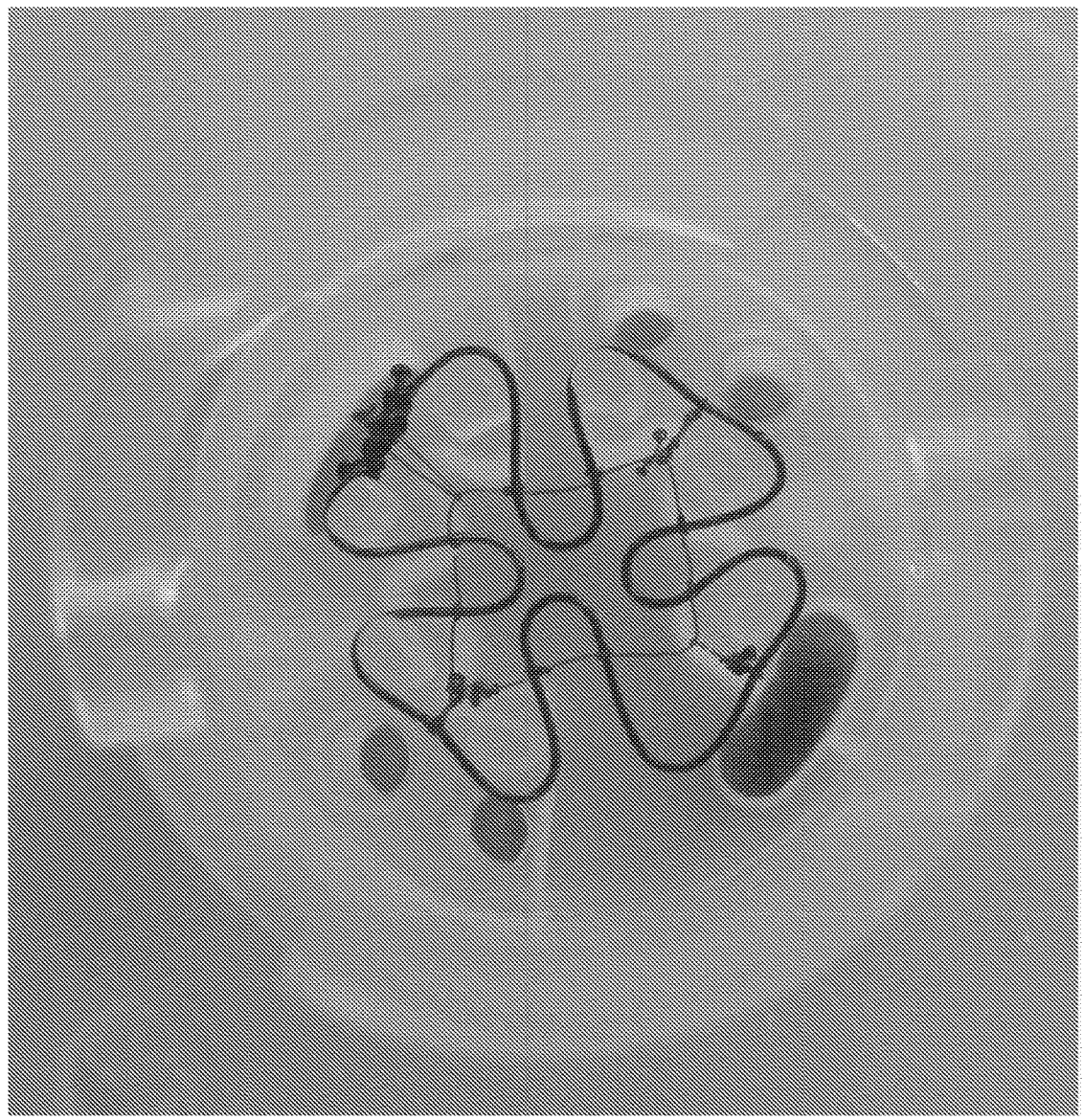

FIG. 10 is a photograph of an experimental model of a haptic design of the invention.

FIG. 11 includes a computer generated image and a schematic to illustrate the relative positions during accommodation of the haptics and a non-flexible optic using the optic holder of the present invention after the fused capsular bag has been sectioned.

FIG. 12 includes a computer generated image and a schematic to illustrate the relative positions of the haptics and non-flexible optic in the unaccommodative state using the optic holder of the invention.

FIG. 13 includes a computer generated image to illustrate radial movement of the haptics when optic holder of the invention is used with a flexible (stretchable) optic.

DETAILED DESCRIPTION OF THE INVENTION

All patent applications, patents and other references cited herein are hereby incorporated by reference in their entirety into the present disclosure.

In ophthalmology, the term "haptic" refers to a support structure that extends out from an optic element of an intraocular lens, for holding the lens in place within the capsular bag of the eye. For purposes of the present invention, "haptics" are sometimes referred to as "zonular capature haptics" and refer to structures or material that not only assist with placement and centration of the lens within the capsule, but are frame-like or fenestrated structures, which permit or facilitate fusion of the anterior and posterior capsules following removal of the natural lens and placement of the artificial lens so that the haptics become securely entrapped within the fused capsule. The haptics define individual "sections" of the capsule which can be separated after fusion has occurred by making radial cuts in the capsule, specifically, beginning near the center and extending out to the equator of the capsule. Following sectioning, each haptic is contained within a separate section of the capsule. The haptics of the optic holder of the invention have features which specifically enable it to become integrated into the fused capsule during fibrosis and then uniformly translate the movement that results from contraction and relaxation of the ciliary body to the optic.

As used herein, the term "retainer" refers to a removable rigid device that is utilized to maintain the IOL system in controlled state of accommodation during the healing, fusion period and is removed once fusion is complete. For example, IOL systems, which rely on angulated haptics as a mechanism of accommodation, would be maintained in an un-accommodated state during fusion of the capsular bag; keeping the optic holder in a flat planar configuration allows maximum contact between the anterior and posterior capsule to enhance fusion and eliminate distortion of the capsular bag. In a single optic system, for example, the retainer may consist of a rigid rod with right angle extension inserting into each diametrically opposed pair of haptics. In a double optic system, a simple suture ligation may be sufficient to maintain the two optics in apposition to each other, reducing the angle of the posterior and anterior haptics to a flat planar configuration. For flexible, prefilled or fillable pouches, the restraining device may be utilized to maintain the IOL system in an accommodated position to encourage the contraction of the capsular bag to a minimum diameter, thereby maximizing the ability of the IOL system to stretch during relaxation of accommodation after the sectioning of the capsular bag.

Such a device may be mechanical or chemical, and may be released by chemical, mechanical, laser or optical means.

As used herein, the term "fenestrated" indicates the presence of an opening or openings that allows for contact between the anterior and posterior capsule thereby facilitating fusion of the capsule through the opening(s).

Conventional accommodating lenses typically involve converting diametral movements of the ciliary muscle into forward and backward movement of an optic portion of the IOL relative to the retina. For example, the only currently marketed accommodating IOL is a rigid, single optic IOL designed to rely on a forward translation of the optic to produce an increase in optical power of the eye. Movement of the IOL is produced by ciliary muscle contraction, capsular bag elasticity and/or suggested changes in vitreous cavity pressure to create an optical change in the eye.

However, implantation of the IOL into the capsule is followed by a natural physiological process not unlike applying a shrink-wrap film, in which the anterior and posterior capsular bag surfaces fuse around the haptics and seal the IOL within the fibrotic capsule. Furthermore, the fusing capsule undergoes fibrosis. During fibrosis the bag undergoes further contraction and loss of elasticity. As a result of this process, the IOL is immobilized within the fibrosed capsular disc and movement of the optic along the optical axis is extremely limited.

The present invention is directed to an optic holder having a haptic system designed to restore capsular flexibility lost during fusion and fibrosis. This haptic system allows an implanted lens to transition more effectively between the accommodated and unaccommodated states, that is, in a fashion similar to the natural lens in response to forces applied to the capsule by the ciliary muscle and zonules. It achieves this by employing a haptic system that is flexible and becomes securely integrated into the fused capsular disc and allows for the capsular disc to be cut into sections, which has the effect of reducing the rigidity of the fused capsular disc and allows the optic holder to expand.

Figure 1A:
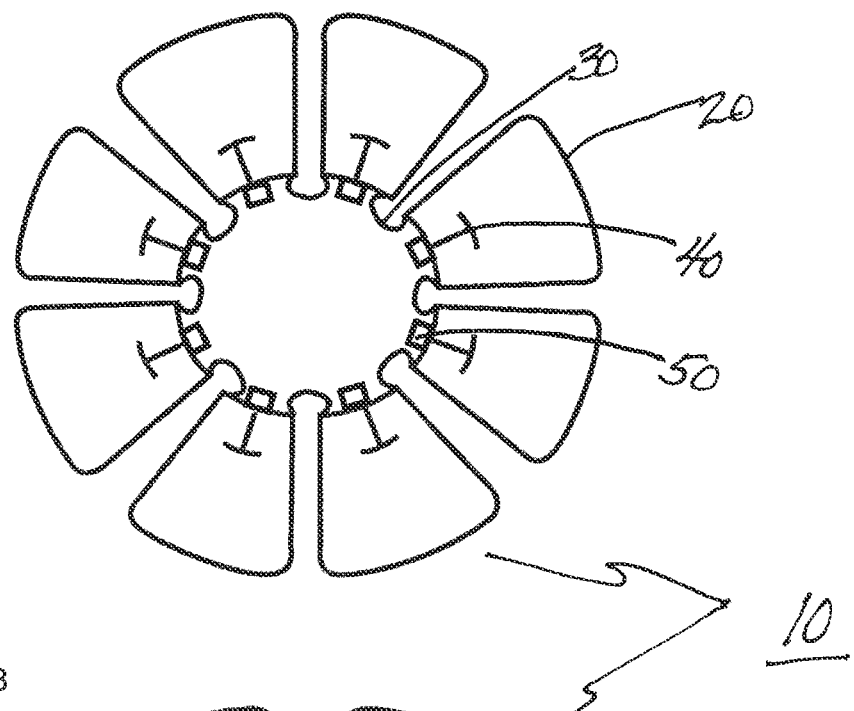
FIGS. 1a and 1b are illustrations of one embodiment of a flexible optic holder of the invention.
Figure 1B:
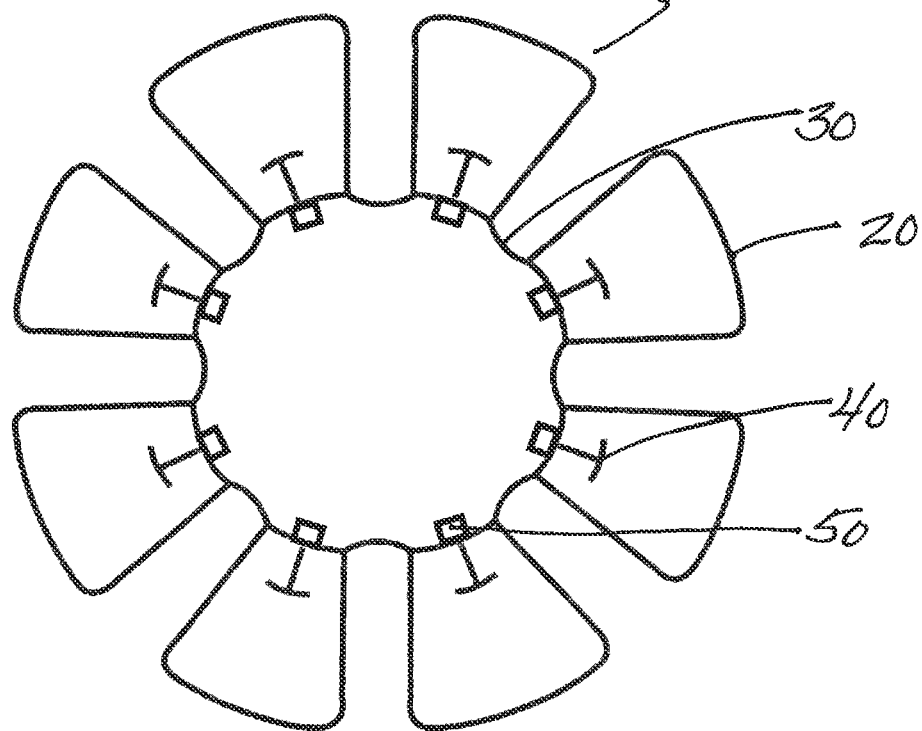

The present invention, therefore, is directed to a flexible optic holder comprising a plurality of haptics arranged in a circle and extending outwardly from a center portion of the optic holder (see FIGS. 1a and 1b). In addition to providing centration of the optic within the capsule like the haptics in conventional intraocular lenses, the haptic system of the optic holder of the present invention provide closed-loop, frame-like structures that allow contact between the anterior and posterior capsules so that the process of capsular fusion and fibrosis are not impeded, thereby creating a skeletal support for the capsular disc. The natural post-phacoemulsification healing process is important for integration of the haptics into the capsular disc. Furthermore, the haptics are regularly arranged around the optic holder ring with a space between adjacent haptics to permit the fused capsular disc to be cut at regular intervals.

The haptics of the optic holder of the invention may be rigid or semi-rigid structures and may be made from a generally continuous element or a single continuous element of varying widths or thicknesses as long as the ability of the anterior and posterior capsules to securely fuse through the haptic is preserved. Haptics are made of a suitable nonabsorbable surgical material such as surgical wire, suture or the like. In one embodiment, haptics are constructed of polypropylene suture material, such as Prolene® (Ethicon, Somerville N.J.) The haptics of the optic holder may optionally include additional structures within the haptic frame, such as cross bars or anchors (for example, as shown in FIG. 1), to reinforce the haptic within the capsule following fusion. Anchors may be T-shaped, or a grid with cross-members that cross the length and/or width of the haptic.

The present invention also provides a two-stage process for inserting into an eye the intraocular lens system of the invention to achieve an improved level of accommodation. In one embodiment, evacuation of the capsular bag is followed by placement within the capsular bag of an optic holder that comprises one or more haptics that define a capsule-reinforcing disc and which will ultimately receive the optic of the IOL system. Implantation of the haptic is followed by a healing interval, that is, a period of time sufficient to allow the anterior and posterior capsular bag surfaces to fuse together through and around the haptics of the optic holder thereby sealing the haptics within the fibrotic capsule. In one embodiment of the method, fusion of the capsular bag around the haptic occurs under conditions in which ciliary body movement is restricted, for example, by atropine-induced cycloplegia or pilocarpine-induced accommodation; paralysis of accommodation movement optimizes capsular disc size, and enhances fibrosis of the capsule. Alternatively, mechanical means for maintaining the capsule in the unaccommodative or accommodative state, for example a retainer, may be employed to achieve the desired capsular disc size. The absence of an accommodating optic during the phase of capsular fusion allows the optic holder to be free of mechanical strain and capsular bag distortion during the fusion and fibrosis period.

During the second stage the capsular disc and incorporated haptics are sectioned to reduce the rigidity of the capsular bag so that the force exerted by the zonules can more effectively be transmitted to the capsule and permit movement of the optic along its optical axis and in the case of flexible optics, accommodative and unaccommodative movement caused by contraction of the ciliary muscle and/or zonular tension. Cuts are made radially and at regular intervals between the haptics, (see FIG. 3) extending from the visual axis to the equator of the capsular disc. The accommodating optic may be inserted into the ring of the optic holder at the time of sectioning, either before or after sectioning. The optic contains means for securing the optic into the lens holder, for example a circumferential releasable connecting rib or series of releasable connecting tabs, pins, plugs or the like that snap into a corresponding receptacle: a groove, notch or hole on the inner edge of the haptic.

The intraocular lens system of the invention comprises a rigid or flexible optic, single lens or multiple lenses, or fillable or pre-filled, and in one embodiment, an accommodating optic and optic holder are inserted as a single unit at the time of initial cataract surgery. Such an integrated intraocular lens system may include a restricting device to mechanically or chemically maintain the system in a specific state of accommodation during the fusion and fibrosis of the capsular disc, for example a maximally accommodated optic and pilocarpine-induced pharmacologic accommodation during the entire duration of capsular fibrosis and fusion. This eliminates mechanical strain or movement or distortion of the capsular bag during the fusion/fibrosis phase after the first stage procedure, optimizing the size of the fibrotic capsular disc, sealing of the haptic members in the capsular disc and resting tension on the zonules.

During the second stage, radial cuts are made in the capsular disc, between the haptics, and extending from the visual axis to the outer edge of the capsular disc. This releases the restraining effect of fibrosis on the now segmented, capsular bag. An optic restraining device, if employed, is also removed at this time allowing the accommodating optic to respond to the zonular tension transmitted by the haptics during relaxation of accommodation, or to return to its resting accommodating state during contraction of ciliary body and relaxation of the zonules.

The method of the present invention for the implantation of an intraocular lens, therefore, includes making a plurality of regularly-spaced radial cuts around the capsule/haptics, extending from the visual axis to the edge of the capsular bag. Sectioning alters the rigidity of the capsule following capsular fibrosis/fusion so that the tension and relaxation of the zonules is more effectively translated to the capsule thereby enhancing spatial displacement of the optical element.

Uniform and complete natural, therapeutically-assisted or -enhanced fusion of the capsule around the haptic prior to optic placement ensures uniformity of sectioning essential to centration and stability of the optic once it is inserted.

Following insertion, the patient undergoes a recovery period of one to six weeks, preferably two to three weeks, for complete fibrosis of the capsule to occur. A second surgical procedure is performed to restore "elasticity" to the capsule by making radial incisions in the capsule at regular intervals forming roughly triangular or trapezoidal sections, each of which contains one of the haptics of the optic holder.

By "sectioning" the capsular disc, greater movement of the optic along the optical axis is achieved. Each haptic-reinforced section of the sectioned disc is generally separate from the others, held together by the inter-haptic connectors of the lens holder and the optic, when it is positioned within the optic holder. As a result of the sectioning, however, the force generated by the zonules is more effectively transmitted to the optic.

It is hypothesized that a 1 mm change in capsular bag diameter results in 2 mm anterior/posterior optic movement. A 12 mm capsular bag under zonular tension, (i.e. unaccommodated) collapsing to 11 mm in diameter as a result of the AIOL tension will result in a 2 mm anterior displacement during accommodation. Expected ranges of total accommodation with rigid single and double optics and flexible deformable optics are shown in Table 1.

TABLE 1

|  | Single Optic | Dual Optic | Flexible Optic |
| --- | --- | --- | --- |
| Actual accommodation | 2D | 6D | 4-7D |
| Pseudo accommodation | 1.5-2D | 1.5-2D | 1.5-2D |
| Total accommodation | 3.5-4D | 7.5-8D | 4.5-9D |

Intraocular Lens System

The intraocular lens system of the invention comprises 1) a flexible optic holder specifically adapted to permit fusion of the capsule and sectioning of the capsular disc once fusion is complete and 2) an optic. The optic holder comprises a plurality of haptics adapted to receive and secure the optic(s). The optic holder supports the optic around its equator and couples the optic to the capsular bag of the eye. Following extraction of the natural lens and placement of the flexible optic holder of the invention into the capsular bag, the natural healing process causes the optic holder to become entrapped, "capturing" the capsule, when the anterior and posterior leaves of the capsular bag fuse together.

Subsequently, radial cuts to the capsule allow the sections of the fused capsule and the captured haptics to move independently of the others in response to zonular tension.

Optic Holder with Zonular Capture Haptics

The intraocular lens of the invention comprises a optic holder with zonular capture haptics, that is, haptics, which by their closed-loop design, allow maximal fusion of the anterior and posterior capsule through the haptics and permit the capsule to be sectioned following fusion, so that, in response to tension by the zonules, each haptic is able to move radially away from the center of the optic holder and then return to the initial position when zonular tension is released. The haptics become fused within the capsular bag and enables the capsule to be sectioned into a plurality of capsular "sections." The haptics provide fixation, centration and stability of the optic(s) within the eye and provide a skeletal support for the capsular bag so that its rigidity can be reduced by cutting it into sections.

One embodiment of an optic holder of the present invention is shown in FIG. 1. Optic holder 10 comprises a plurality of haptics 20 extending outwardly from the center of optic holder 10. The arrangement of haptics 20 generally defines a ring that receives an optic 80, and haptics 20 further comprise optic attachment means 50/52 to hold the optic 80 securely in place. In this embodiment, haptics 20 are roughly trapezoidal in shape. Adjacent haptics 20 are connected via an inter-haptic loop or connector 30 of flexible material so that the inner edges of haptics 20 form a continuous ring to which the optic is ultimately attached.

In some embodiments, optic holder 10 is flexible (FIG. 1b). The haptics 20 are spaced apart at regular intervals to generally form a disc that is roughly coextensive in size with the capsular bag and retains the circular shape of the fused capsular disc. Following placement of an optic holder of the invention into the capsular bag, the capsule will shrink and fuse around the optic holder (much like shrink-wrap). As shown in FIG. 2b, once fusion of the capsule is complete, cuts are made between the haptics of the optic holder. This allows the sections to move somewhat independently of each other.

FIG. 2a shows an embodiment of an optic holder of the invention within the unsectioned capsular bag (shaded area). Following sectioning between haptics (FIG. 2b), the optic experiences improved freedom of movement, compared to the unsectioned capsule in response to zonular tension.

Figure 3:
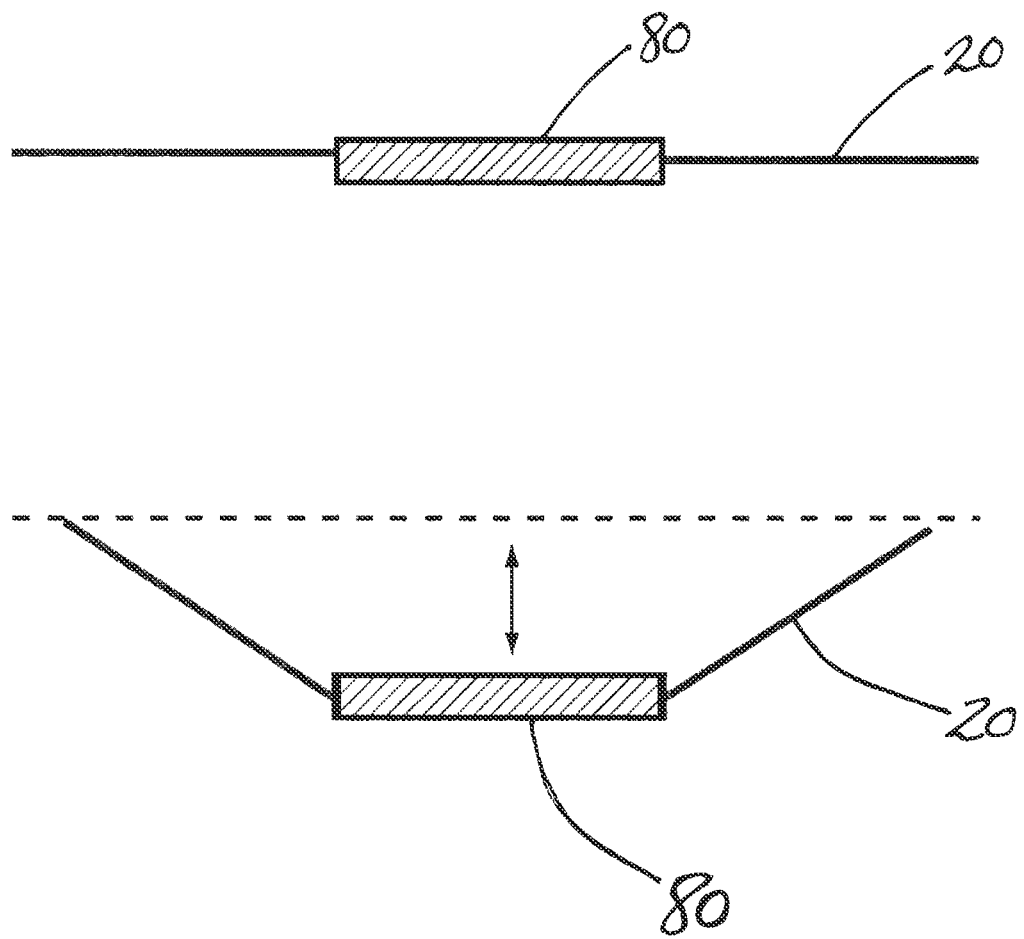
FIG. 3 is a schematic showing the position of the optic in the unaccommodated (top) and accommodated (bottom) states. During accommodation, the optic moves anteriorly (shown as downward); the dotted line indicates the position to which the optic returns when in the unaccommodated position.

In FIG. 3, the positions of the haptics and optic of any intraocular lens, including conventional intraocular lenses, once the capsule has fused and become fibrosed are shown in the upper panel. The bottom panel shows anterior movement of the optic (shown as downward movement) made possible by sectioning the fused capsule using the optic holder of the present invention.

FIG. 4a shows an embodiment of an optic holder 100 in which an optic 180 has been secured prior to sectioning of the capsular bag; sectioning lines 184 are indicated. The position of the optic 180 and haptics 120 during accommodation (4b) and the unaccommodative state (4c) are shown.

FIG. 5 shows an embodiment of optic attachment means 52/50, for example, a pin 52 and receptacle 50 snap-like fastener, by which optic 80 is secured in optic holder. Because the haptics are angulated, without any other force in play, insertion of the optic into the holder forces the haptic into a roughly 30° angle with the optic.

In one embodiment (see FIGS. 6 and 7), a pair of anteriorly- and posteriorly-angled optic holders are used in an alternating arrangement or configuration. The anterior haptic will receive an anterior optic, while the posterior one will receive a posterior optic. In the dual-optic system, during accommodation, zonular tension is released and the haptic system returns to its resting state of maximum angulation of the optic attachment means causing the two lenses to move axially away from each other, thereby providing increased accommodative amplitude.

When tension is applied to the optic holder during relaxation of ciliary body, the haptics straighten thereby causing an axial displacement of the optics towards each other (as shown in FIG. 7c). With a dual-optic system, maintenance of the appositional relationship of anterior and posterior optics is important to ensure uniform fusion of the capsule. This may be achieved mechanically or through the use of therapeutic agents that induce unaccommodation.

Figure 8:
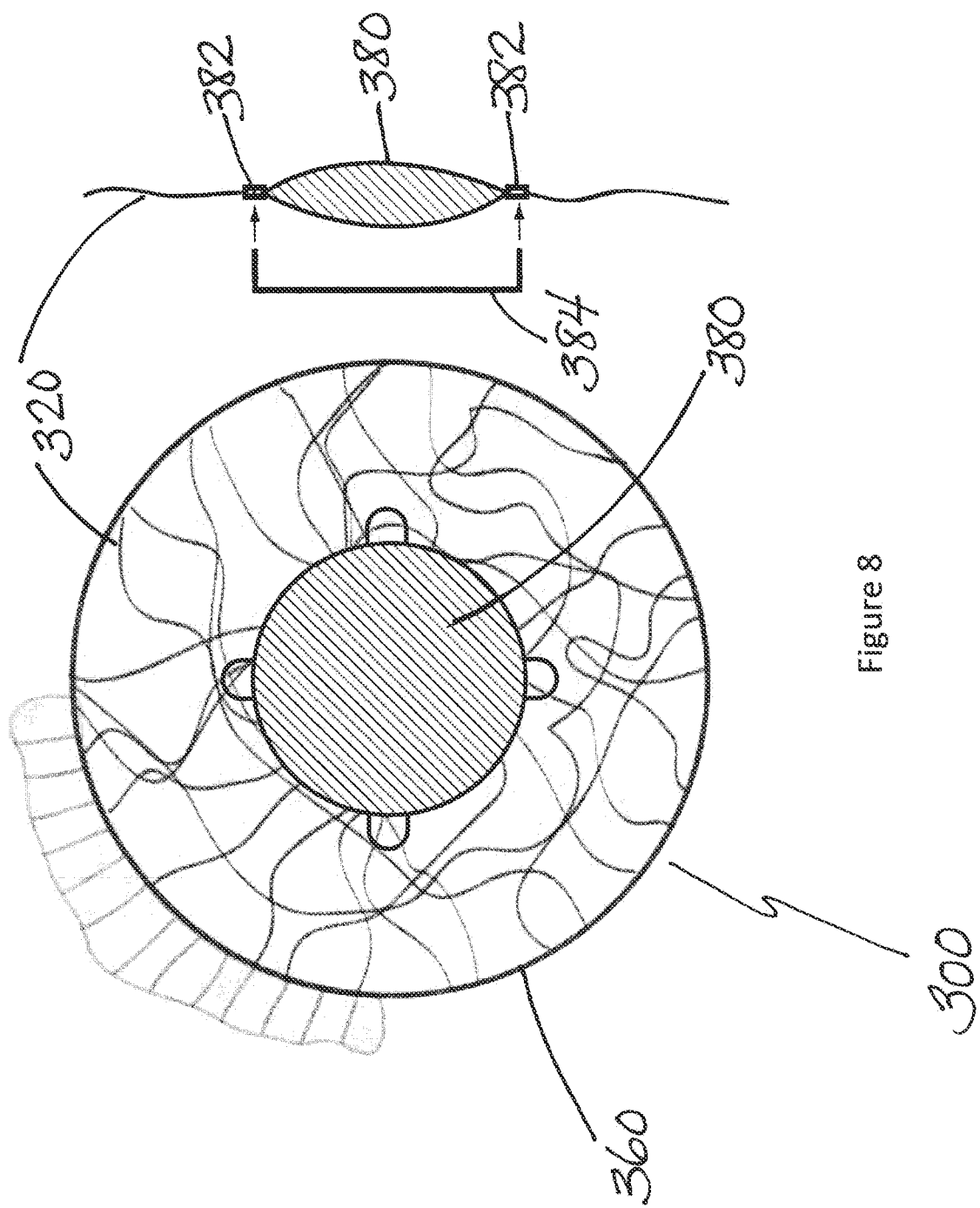
FIG. 8 is an embodiment of an optic holder with a single dough-nut shaped haptic made of a woven or mesh-like material that can be cut, for example, with surgical scissors. A side view of the optic/optic holder is shown with a retainer, mechanical means for maintaining the minimum diameter (maximum contraction) of the capsular bag during fusion.

Referring to FIG. 8, in one embodiment, the optic holder 300 comprises an optic 380 or optic holding member at its center and a single doughnut-shaped haptic 320 extends outwardly from the optic 380 and is made of a woven material or mesh or fenestrated material that 1) permits fusion of the capsular bag and 2) can be sectioned or cut. The optic holder 300 may be kept in an un-accommodated state during fusion of the capsular bag by inserting retainer 384, consisting of a rigid rod with right angle extensions, into the small holes 382 near the optic/optic holding member. Radial sectioning lines (not shown) may be indicated on the capsule-capture haptic and the small holes 382 near the optic/optic holding member provided for starting the cut.

Figure 9B:
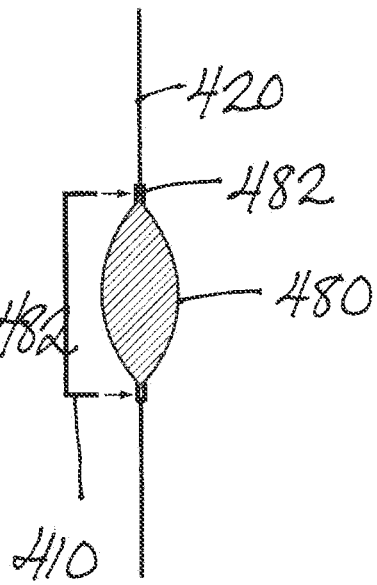
FIG. 9a shows an embodiment of the optic holder with an integrated flexible optic that approximates the natural lens.
Figure 9A:
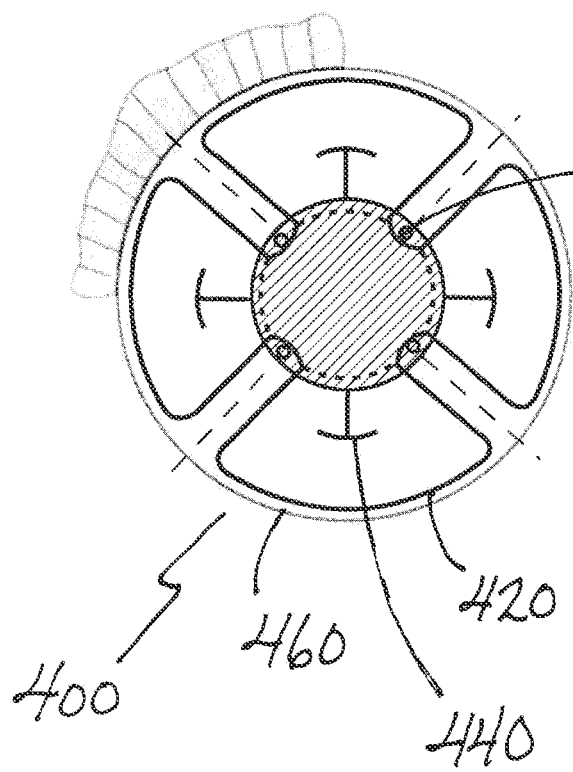
Figure 9C:

FIG. 9 shows an embodiment in which haptics 420 and optic 480 comprise a single unit, with a flexible optic 480, or fillable or prefilled optic pouch attached directly to the haptics 420. Such an optic has a predetermined dioptric power in its resting state (9b). The inherent optic elasticity allows stretching of the optic equator and flattening of the lens curvature in the un-accomodative state (9c) and return to a more spherical shape (9b) during accommodation when zonular tension is released.

Flexible optics, fillable or prefilled optic pouches are known in the art and can be integrated or adapted for use with the optic holder of the invention. The adaptation of any elastic optic embodiments to a zonular capture optic holder would enable the optic to change shape and accommodate.

In some embodiments, the haptics further comprise an anchor or other support structure for promoting fusion/fibrosis of the capsular bag and integration of the haptic within the capsular bag. The anchor may be any shape, for example, T-shaped, or size which will have the effect of securing and reinforcing the haptic within the capsular bag.

Implantation of the Optic Holder

In an initial procedure, the optic holder is placed in the capsular bag of the eye, and the anterior and posterior leaves of the capsular bag are allowed to fuse together securing the optic holder within the fused capsular bag or disc. Uniform healing of capsule around optic holder ensures centration of the optic once it is placed in optic holder.

In a second procedure, a number of cuts are made in the capsular disc between the haptics of the optic holder. The cuts extend from the visual axis to the outer edge of the capsular disc. Additionally, the posterior zonules may become stiff further limiting anterior/posterior movement. In some situations, it may be desirable to cut the posterior zonules.

In one embodiment, the optic holder comprises a ring structure in which at least three capsule-capture members (haptics) extend outwardly from the center of the ring (see FIG. 1). The number and size of capsule-capture members of the optic holder varies depending on the number of sections which the clinician determines to be optimal. In so determining, an optimal number of sections may be determined to be that number which will permit the greatest axial movement of the optic that can be achieved without compromising the integrity of the capsular bag. Further considerations regarding the number of sections to be made include allocating an amount of time for sectioning which the clinician feels is appropriate for the safety and well-being of the patient.

The haptics of the optic holder are made from inert or biocompatible materials known to those of skill in the art, for example, silicone, polypropylene, acrylic polymers or the like. Haptics are made in an open configuration (loops), and may be of any shape, for example, generally triangular or trapezoidal, which, as a group roughly define a disc that is coextensive with the capsular bag. Generally, the outer edge of the haptics extend to the equator of the capsular bag to form a capsule-reinforcing disc which is roughly coextensive with the capsular disc, and by virtue of their shape or porosity, permit fusion of the anterior and posterior leaves of the capsular bag to form a capsular disc encasing the haptic.

The number and configuration of individual members are chosen in accordance with considerations discussed supra to anchor the optic-holder ring in the capsular bag and form an internal "frame" on which the fused capsular disc is supported. To maximize or minimize the diameter of capsular bag during fusion thereby impacting the ultimate size of the fused capsular disc, accommodation can be controlled during fusion of the capsular bag by administration of an agent to inhibit or induce accommodation.

Optics

The intraocular lens system of the invention may comprise multiple lens holders and therefore, be able to hold one or more optics. Optics are generally symmetrical about the optical axis. Examples of suitable optics are well known in the art and can be adapted for use with the optic holder and zonular capture haptics of the invention. These include optics that are flexible, deformable, foldable, or rigid, preformed or fillable and which are made from a liquid, solid or semi-solid material. In one embodiment, if a flexible optic is used, it can assist in accommodation not only by anterior-posterior displacement, but also by changing its radius of curvature.

Examples of suitable optic materials include silicone(s), acrylics, hydrogels and other inert or biocompatible polymers known to those of skill in the art. In one embodiment, the optic comprises a means for securing the optic into the haptic, for example a circumferential releasable connecting rib or series of releasable connecting tabs or pins that snap into a corresponding groove, notch or hole on the haptic.

Haptics may incorporate any means suitable for attaching and securing the optic; these are well known in the art.

Sectioning of capsular disc after fusion and fibrosis of the haptic therein can be accomplished by virtue of a small gauge (for example, 23 or 25 gauge) trans-conjunctival vitrectomy system with trocars and cannulas placed diametrically opposed to the section line in the capsule/haptic where the section is to be made. A small gauge (for example, 23 or 25 gauge) scissor is introduced through a cannula and used to cut the capsule from the visual axis to the outer edge of the capsular disc.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

A haptic arrangement was manufactured from 4-0 surgical Prolene sutures with 7-0 surgical Prolene retention bands (FIG. 10). The function of the retention bands are to maintain the shape of each haptic loop, to function as an additional retaining anchor within each haptic and to maintain the distance between the haptics during the sterilization process. The surgical procedure for implantation of an optic holder of the invention consists of two stages.

All procedures related to the use of animals conform to the Guide for the Care and Use of Laboratory Animals (National Institutes of Health, National Research Council) and are approved by the Wisconsin National Primate Research Center. The animals are housed in facilities accredited by the Association for Assessment and Accreditation of Laboratory Animal Care International (AAALAC). Animal subjects are paired or individually housed. Diet consists of monkey chow supplemented with fresh fruit and vegetables. Water is freely available. All animals are observed daily by a veterinary technical staff and caretakers for signs of ill health.

Adult Rhesus monkeys (*Macacca mulatta*) of either sex without any ocular disease, are the subjects of the following experiments.

At Stage 1, the treated eye is rendered aniridic by complete surgical removal of the iris. The absence of the iris facilitates evaluation of the optic holder's performance. Standard cataract removal by small, clear corneal incision and phacoemulsification is followed by implantation of the lens holder of the invention via standard 2 mm lens injector (Photo 2). The treated eye is maintained in a pharmacologic state of forced accommodation by the administration of pilocarpine drops 4 times per day. This allows the zonules to be free of tension during the healing, fibrosis, contracture phase of the capsular bag. A minimum capsular disc size is thus obtained, which is anticipated to securely incorporate the haptics of the lens holder in between the fused anterior and posterior capsules. Once the fibrosis phase is complete, approximately 2-4 weeks after the Stage 1 surgery, the animal is anesthetized again for the Stage 2 surgery.

A 23 or 25 gauge standard vitrectomy instrument is employed. Four trans-conjunctival cannulas are inserted at the standard pars plana location, coinciding with the planned capsular section lines as defined by the location of the spaces between the haptics. A central posterior capsulotomy is performed with the vitrectomy instrument. A 23 or 25 gauge Vitrcoretinal scissor is introduced via each cannula to perform radial cuts extending from the edge of the posterior capsulotomy to the equator of the capsular bag, cutting across the fused capsular sheets, the 7-0 Prolene suture extending in between capsular members, to the edge of the capsular disc, ensuring that no connection remains between the individual sections of capsular disc capsule. The only connection between the sectioned capsules and entrapped haptics is the flexible inter-haptic loop extending from one haptic to the next.

Administration of pilocarpine drops is discontinued postoperatively. Once the eye has recovered from the surgical intervention, the eye is challenged with pharmacologic accommodation and relaxation of accommodation under anesthesia with short acting pharmacologic agents while the eye is monitored and videographed. It is anticipated that during relaxation of accommodation, zonular tension is produced and transmitted to the individual segments of the former capsular disc, which now move independently. Each haptic of the optic holder should move centrifugally and away from each other. When accommodation is induced pharmacologically, the tension of the zonules is released and the elasticity of the inter-haptic loops returns haptics to a closer configuration. A change in diameter of the optic holder of up to 1 mm is expected, based on previously published data.

I claim:

1. An intraocular lens system comprising:
   an optic holder comprising a plurality of radially disposed haptics adapted to move independently in response to forces of at least one of a ciliary muscle and zonules of an eye when implanted,
   wherein (i) said haptics are closed-loops, thereby allowing fusion of a capsular bag through the haptics so that the haptics are configured to become fixed within the capsular bag, (ii) each closed-loop haptic is formed from at least one of a surgical wire or a suture, (iii) said plurality of haptics comprises at least three outwardly extending haptics defining sectioning intervals therebetween, said plurality of haptics being at least one of trapezoidal or regularly spaced, and (iv) outer segments of the plurality of haptics collectively define a circular disc.

2. The optic holder of claim 1, wherein said haptics are rigid or semi-rigid.

3. The optic holder of claim 1, where said plurality of haptics comprises no more than 120 haptics.

4. The intraocular lens system of claim 1, further comprising:
   an optic coupled to the plurality of haptics.

5. The intraocular lens system of claim 1, further comprising a mechanical restricting device configured to maintain the closed-loop haptics in a specific state of accommodation.

6. The intraocular lens system of claim 1, further comprising a retainer adapted to achieve a desired capsular disc size.

7. The intraocular lens system of claim 1, wherein the circular disc is configured to be coextensive with an equator of the capsular bag.

8. An optic holder consisting essentially of:
   at least one optic holding member; and
   a single annular uncut haptic extending from the at least one optic holding member, the single uncut annular haptic configured to be implanted into an eye, the single uncut annular haptic configured to be cut into sections after fusion of a capsular bag of the eye, the sections being adapted to move in response to forces of at least one of a ciliary muscle and zonules of the eye.

9. The optic holder of claim 8, wherein said haptic comprises cutting lines indicated thereon.

10. An intraocular lens system comprising:
    an optic holder comprising a plurality of radially disposed haptics adapted to move independently in response to forces of at least one of a ciliary muscle and zonules of an eye when implanted,
    wherein (i) said haptics are closed-loops, thereby allowing fusion of a capsular bag through the haptics so that the haptics are configured to become fixed within the capsular bag (ii) each closed-loop haptic is formed from a surgical wire, (iii) outer segments of the plurality of haptics collectively define a circular disc, and (iv) where said plurality of haptics comprises at least three outwardly extending haptics.

11. The optic holder of claim 10, wherein each of said haptics are regularly spaced defining sectioning intervals therebetween.

12. The intraocular lens system of claim 10, wherein the circular disc is configured to be coextensive with an equator of the capsular bag.

* * * * *